United States Patent
Sun et al.

(10) Patent No.: US 10,945,993 B2
(45) Date of Patent: Mar. 16, 2021

(54) METHODS OF RECRUITING SDF-PRODUCING MACROPHAGES

(71) Applicant: MedRegen, LLC, Baltimore, MD (US)

(72) Inventors: Zhaoli Sun, Perry Hall, MD (US); George Melville Williams, Stuart, FL (US); Qing Lin, Baltimore, MD (US)

(73) Assignee: MedRegen, LLC, Baltimore, MD (US)

( * ) Notice: Subject to any disclaimer, the term of this patent is extended or adjusted under 35 U.S.C. 154(b) by 0 days.

(21) Appl. No.: 14/787,164

(22) PCT Filed: Apr. 29, 2014

(86) PCT No.: PCT/US2014/035793
§ 371 (c)(1),
(2) Date: Oct. 26, 2015

(87) PCT Pub. No.: WO2014/179266
PCT Pub. Date: Nov. 6, 2014

(65) Prior Publication Data
US 2016/0106710 A1 Apr. 21, 2016

Related U.S. Application Data

(60) Provisional application No. 61/816,827, filed on Apr. 29, 2013, provisional application No. 61/907,624, filed on Nov. 22, 2013.

(51) Int. Cl.
| | | |
|---|---|---|
| *A61K 31/395* | (2006.01) | |
| *A61K 31/436* | (2006.01) | |
| *A61K 31/4427* | (2006.01) | |
| *A61K 31/5377* | (2006.01) | |
| *A61K 38/19* | (2006.01) | |
| *A61K 38/18* | (2006.01) | |
| *A61K 38/13* | (2006.01) | |
| *A61P 17/02* | (2006.01) | |
| *A61K 45/06* | (2006.01) | |

(52) U.S. Cl.
CPC .......... *A61K 31/395* (2013.01); *A61K 31/436* (2013.01); *A61K 31/4427* (2013.01); *A61K 31/5377* (2013.01); *A61K 38/13* (2013.01); *A61K 38/18* (2013.01); *A61K 38/193* (2013.01); *A61K 45/06* (2013.01); *A61P 17/02* (2018.01)

(58) Field of Classification Search
None
See application file for complete search history.

(56) References Cited

U.S. PATENT DOCUMENTS

| | | | |
|---|---|---|---|
| 5,365,948 | A | 11/1994 | McMichael |
| 6,825,351 | B2 | 11/2004 | McEachern et al. |
| 6,835,731 | B2 | 12/2004 | Bridger et al. |
| 7,943,744 | B2 | 5/2011 | Frendeus et al. |
| 2005/0058622 | A1 | 3/2005 | Lyman et al. |
| 2007/0190023 | A1 | 8/2007 | Battista et al. |
| 2008/0009495 | A1 | 1/2008 | Kokubo et al. |
| 2008/0038269 | A1 | 2/2008 | Susan |
| 2010/0105717 | A1 | 4/2010 | Gordon et al. |
| 2010/0226894 | A1 | 9/2010 | Yeung et al. |
| 2013/0052231 | A1 | 2/2013 | Sun et al. |
| 2013/0202553 | A1 | 8/2013 | Zheng |
| 2013/0338183 | A1 | 12/2013 | Sun et al. |

FOREIGN PATENT DOCUMENTS

| | | |
|---|---|---|
| EP | 1693065 A1 | 8/2006 |
| WO | 2005/020993 A1 | 3/2005 |
| WO | 2006/123226 A2 | 11/2006 |
| WO | 2009/037093 A1 | 3/2009 |
| WO | 2009/074807 A2 | 6/2009 |
| WO | 2009/094456 A2 | 7/2009 |
| WO | 2010/022017 A2 | 2/2010 |
| WO | 2010/029185 A1 | 3/2010 |
| WO | 2010/054271 A1 | 5/2010 |
| WO | 2010/093802 A2 | 8/2010 |
| WO | 2011/072216 A2 | 6/2011 |
| WO | 2012/078746 A2 | 6/2012 |

OTHER PUBLICATIONS

Wagner, JE, et al., (2010) Bone marrow transplantation for recessive dystrophic epidermolysis bullosa. N Engl J Med 363:629-39.

Fathke, C, et al., (2004) Contribution of bone marrowderived cells to skin: collagen deposition and wound repair. Stem Cells 22:812-22.

Ishii G, et al., (2005) "In vivo characterization of bone marrow-derived fibroblasts recruited into fibrotic lesions" Stem Cells 23:699-706.

Korbling, M, et al., (2002) "Hepatocytes and epithelial cells of donor origin in recipients of peripheral-blood stem cells" N Engl J Med 346:738-46.

Chino, T, et al., (2008) "Bone marrow cell transfer into fetal circulation can ameliorate genetic skin diseases by providing fibroblasts to the skin and inducing immune tolerance" Am J Pathol 173:803-14.

Cerqueira M, et al., (2012) Using stem cells in skin regeneration: possibilities and reality Stem Cells Dev 21:1201-14.

Devine, SM, et al., (2004) Rapid mobilization of CD34Þ cells following administration of the CXCR4 antagonist AMD3100 to patients with multiple myeloma and non-Hodgkin's lymphoma J Clin Oncol 22:1095-102.

Jujo, K, et al., (2010) CXCR4 blockade augments bone marrow progenitor cell recruitment to the neovasculature and reduces mortality after myocardial infarction. Proc Natl Acad Sci USA 107:11008-13.

(Continued)

*Primary Examiner* — Elly-Gerald Stoica

(74) *Attorney, Agent, or Firm* — DLA Piper LLP (US)

(57) ABSTRACT

The present invention relates to the field of wound healing. More specifically, the present invention provides methods and compositions useful for improved wound healing via autologous stem cell mobilization. In one embodiment, a method for improving wound healing in a patient comprises administering to the patient a therapeutically effective amount of a stem cell mobilizer and a low dose of an immunosuppressive agent.

12 Claims, 24 Drawing Sheets

Specification includes a Sequence Listing.

(56) References Cited

OTHER PUBLICATIONS

Jujo, K, et al., (2013) CXC-chemokine receptor 4 antagonist AMD3100 promotes cardiac functional recovery after ischemia/reperfusion injury via endothelial nitric oxide synthase-dependent mechanism. Circulation 127:63-73.
Nishimura, Y, et al., (2012) CXCR4 antagonist AMD3100 accelerates impaired wound healing in diabetic mice. J Invest Dermatol 132:711-20.
Staatz, C., et al., "Clinical pharmacokinetics and pharmacodynamics of tacrolimus in solid organ transplantation", Clin Phyarmacokinet 2004, vol. 43, No. 10, pp. 623-653.
Bai, L, et al., (2010) Low- but not high-dose FK506 treatment confers atheroprotection due to alternative macrophage activation and unaffected cholesterol levels. Thromb Haemost 104:143-50.
Nishino, T, et al., (1995) Hepatocyte growth factor as a hematopoietic regulator. Blood 85:3093-100.
Ding, S, et al., (2003) HGF receptor up-regulation contributes to the angiogenic phenotype of human endothelial cells and promotes angiogenesis in vitro. Blood 101:4816-22.
Neuss, et al., (2004) Functional expression of HGF and HGF receptor/c-met in adult human mesenchymal stem cells suggests a role in cell mobilization, tissue repair, and wound healing. Stem Cells 22:405-14.
Sun G, et al., (2011) Dextran hydrogel scaffolds enhance angiogenic responses and promote complete skin regeneration during burn wound healing. Proc Natl Acad Sci USA 108:20976-81.
Hollemann, D, et al., (2012) New vessel formation in peritumoral area of squamous cell carcinoma of the head and neck. Head Neck 34:813-20.
Ito, M, et al., (2005) Stem cells in the hair follicle bulge contribute to wound repair but not to homeostasis of the epidermis. Nat Med 11:1351-4.
Ito, M, et al., (2007) Wnt-dependent de novo hair follicle regeneration in adult mouse skin after wounding. Nature 447:316-20.
Charruyer, A, et al., (2012) CD133 is a marker for long-term repopulating murine epidermal stem cells. J Invest Dermatol 132:2522-33.
Gay, D, et al., (2013) Fgf9 from dermal gd T cells induces hair follicle neogenesis after wounding. Nat Med 19:916-23.
Fuchs, Y, et al., (2013) Sept4/ARTS regulates stem cell apoptosis and skin regeneration. Science 341:286-9.
Francavilla, A., et al., "Augmentation of rat liver regeneration by FK 506 compared with cyclosporin", The Lancet, 1248-1249, Nov. 25,1989.
Tamura, F., et al., "FK506 promotes liver regeneration by suppressing natural killer cell activity", Journal of Gastroenterology and Hepatology, 13,703-708 (1998).
Francavilla, A., et al., "Studies on mechanisms of augmentation of liver regeneration by cyclosporine and FK 506", Hepatology, 14(1) 140-143 (Jul. 1991).
Nishinaka, Y., et al., "Protective effect of FK506 on ischemia/reperfusion-induced myocardial damage in canine heart", Journal of Cardiovascular Pharmacology, 21(3), 448-454 (1993).
Sakr, M., et al., "FK 506 pre-treatment is associated with reduced levels of tumor necrosis factor and interleukin 6 following hepatic ischemia/reperfusion", Journal of Hepatology, 17: 301-307 (1993).
Van Thiel, D., et al., "FK 506 reduces the injury experienced following renal ischemia and reperfusion" Renal Failure, 14(3), 285-288 (1992).
Choi, H., et al., Plerixafor for stem cell mobilization in patients with non-hodgkin's lymphoma and multiple myeloma, Annals of Pharmacotherapy, 44(1), 117-126 (2010).
Davies, S., et al., "Plerixafor Hydrochloride" Drugs of the Future, Jan. 1, 2007, vol. 32, No. 2, pp. 123-136.
Pento, J., "FK-506", Drugs of the Future, Jan. 1, 1989, vol. 14, No. 8, pp. 746-752.
Search Report dated Jul. 18, 2013 for EP application 108367467.
Margarit, C., et al., "Efficacy and safety of oral low-dose tacrolimus treatment in liver transplantation", Transplant International (1998) vol. 11, Suppl. 1, pp. S260-S266.
Podesser, B., et al., "Comparison of low and high initial tacrolimus dosing in primary heart transplant recipients: a prospective european multicenter study", Transplantation, Jan. 15, 2005, vol. 79, No. 1, pp. 65-71.
Muramatsu, K., et al., "Prolonged survival of experimental extremity allografts: a new protocol with total body irradiation, granulocyte-colony stimulation factor, and FK506", Journal of Orthopaedic Research, (online: Oct. 29, 2009) vol. 28, No. 4, pp. 457.
Okabayashi, T., et al., "Mobilization of hose stem cells enables long-term liver transplant acceptance in a strongly rejecting rat strain combination", American Journal of Transplantation, Oct. 2011, vol. 11, No. 10, pp. 2046-2056.
Search Report dated Apr. 4, 2014 for EP Application 118461938.
Pelus, "Peripheral blood stem cell mobilization: new regimens, new cells, where do we stand", Curr Opin Hematol, Jul. 2008, vol. 15, No. 4, pp. 285-292.
Broxmeyer, H., et al., "Rapid mobilization of murine and human hematopoietic stem and progenitor cells with AMD3100, a CXCR4 antagonist", JEM, Apr. 18, 2005, vol. 201, No. 8, pp. 1307-1318.
Notification of the Second Office Action dated Jan. 4, 2018, of corresponding Chinese Application No. 201480037499.1, along with an English translation.
Mandelin, J.M. et al., "Leg Ulcers Treated with Topical Tacrolimus in Patients with Rheumatoid Arthritis", Acta Dermato-Venereologica, vol. 90, No. 6, 2010, pp. 633-634.
Teruo, Kiyama et al., "Tacrolimus enhances colon anastomotic healing in rats", Wound Repair and Regneration, vol. 10, No. 5, 2002, pp. 308-313.
Extended European Search Report from counterpart EP Patent Appln. No. 14791563 dated Jul. 3, 2019.
Communication pursuant to Article 94(3) EPC from counterpart European Appln. No. 14791563.1 dated Jul. 24, 2020.
Nair, Anroopb et al., "A simple practice guide for dose conversion between animals and human",*Journal of Basic and Clinical Pharmacy*, vol. 7, No. 2, Jan. 1, 2016, pp. 27-31.

LEFT RIGHT

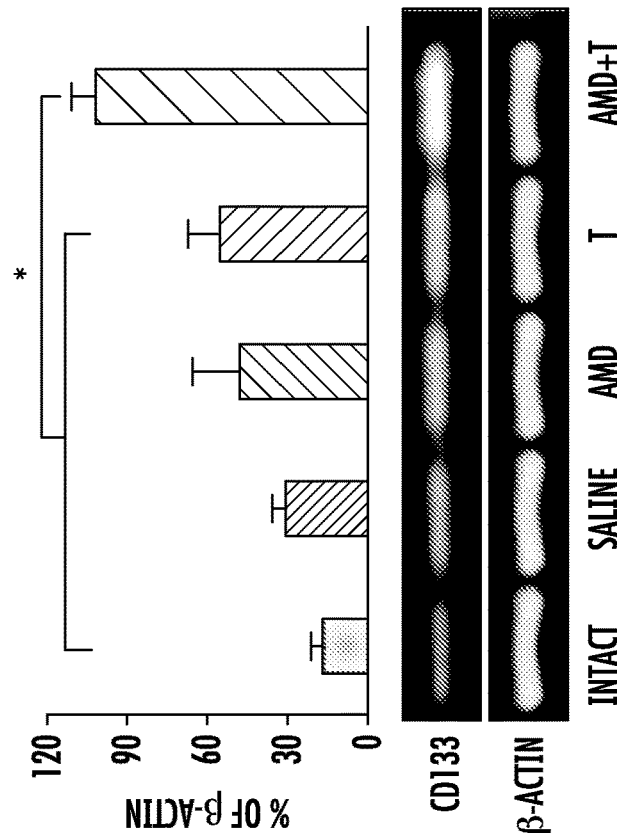
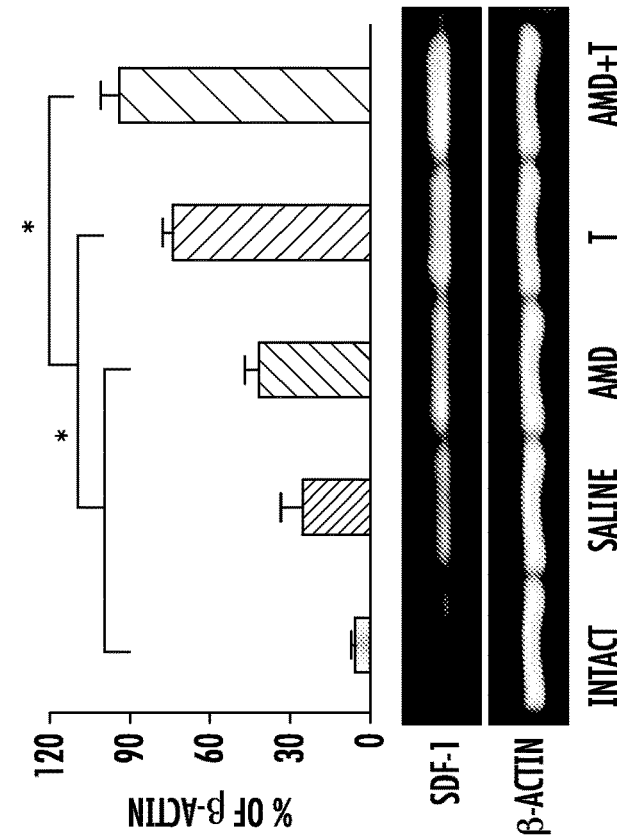
FIG. 4A
FIG. 4B

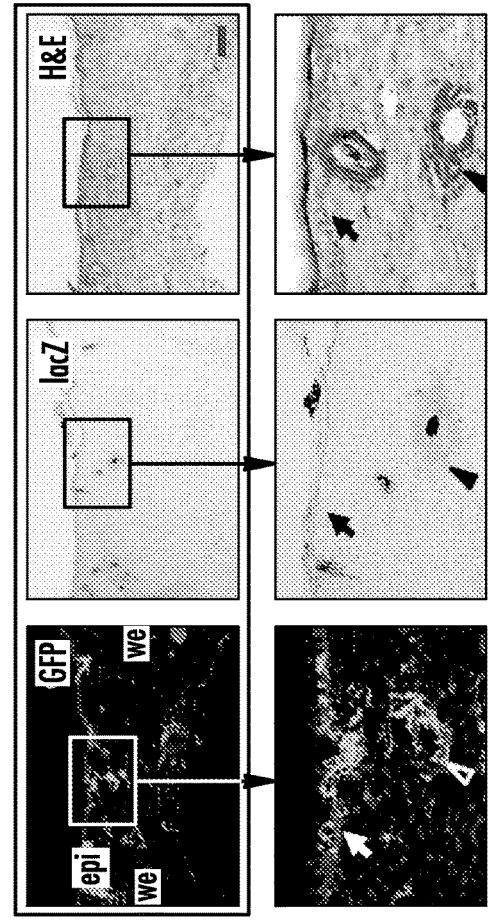
FIG. 6C
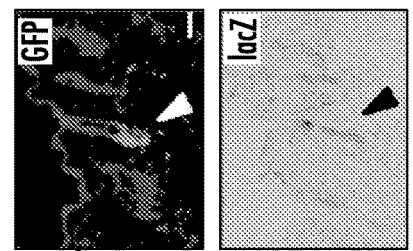
FIG. 6D
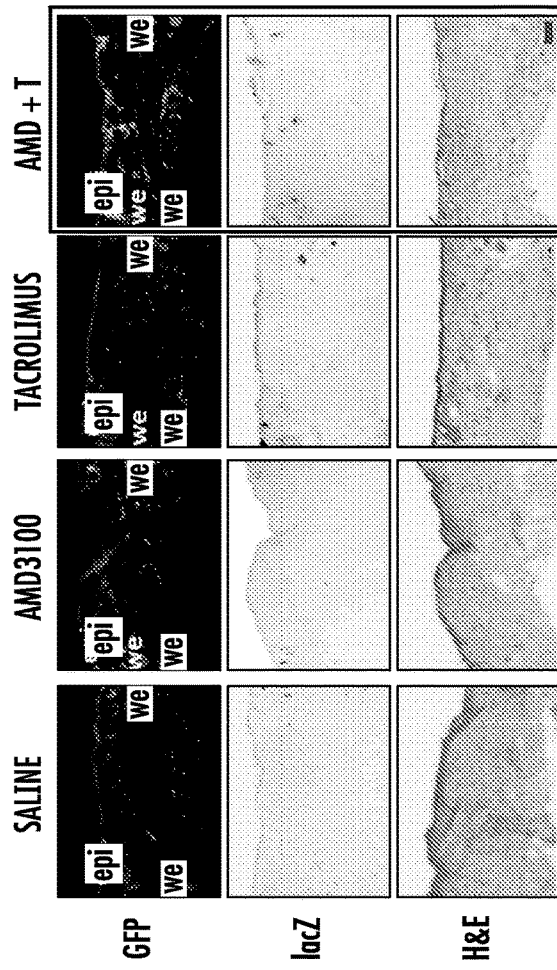
FIG. 6A
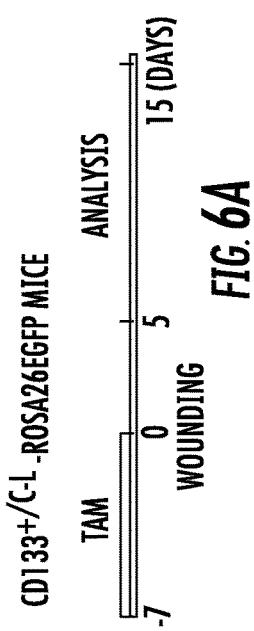
FIG. 6B
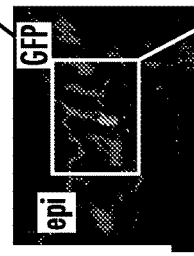

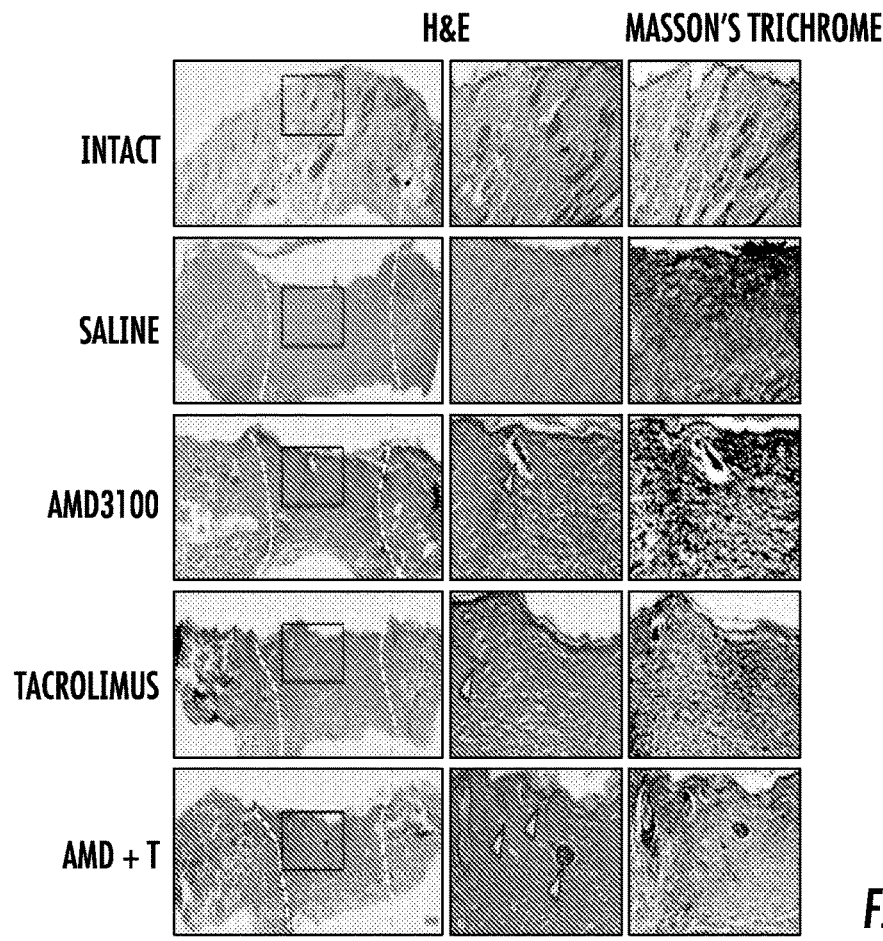
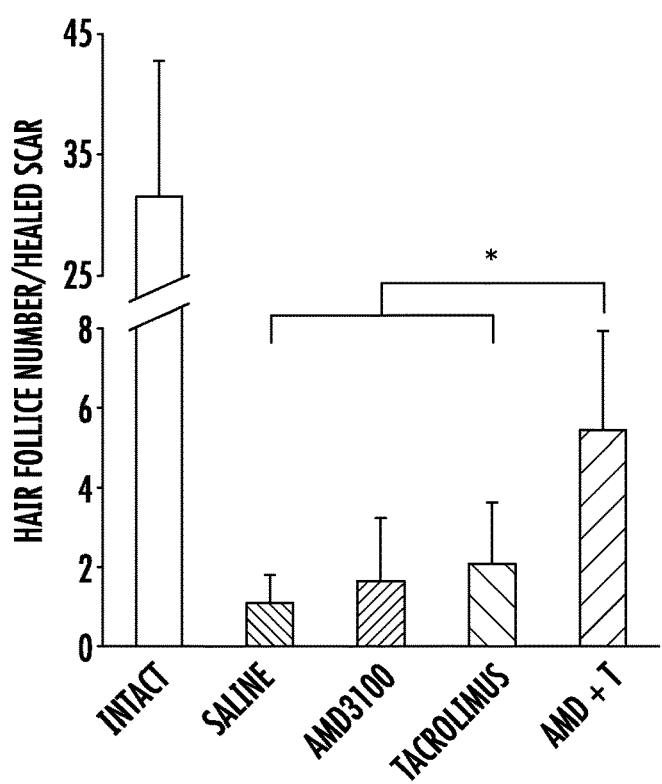
FIG. 9A
FIG. 9B

METHODS OF RECRUITING SDF-PRODUCING MACROPHAGES

CROSS-REFERENCE TO RELATED APPLICATIONS

This application is a 35 U.S.C. § 371 U.S. national entry of International Application PCT/US2014/035793, having an international filing date of Apr. 29, 2014, which claims the benefit of U.S. Provisional Application No. 61/816,827, filed Apr. 29, 2013, and U.S. Provisional Application No. 61/907,624, filed Nov. 22, 2013, the content of each of the aforementioned applications is herein incorporated by reference in their entirety.

FIELD OF THE INVENTION

The present invention relates to the field of wound healing. More specifically, the present invention provides methods and compositions useful for improved wound healing via autologous stem cell mobilization.

INCORPORATION-BY-REFERENCE OF MATERIAL SUBMITTED ELECTRONICALLY

This application contains a sequence listing. It has been submitted electronically via EFS-Web as an ASCII text file entitled "P12415-03_ST25.txt." The sequence listing is 2,713 bytes in size, and was created on Apr. 24, 2014. It is hereby incorporated by reference in its entirety.

BACKGROUND OF THE INVENTION

More than 1.25 million people suffer burns and 6.5 million have chronic skin ulcers caused by pressure, venous stasis, or diabetes mellitus every year in the United States (Singer and Clark, 1999). The treatment of these conditions remains imperfect and expensive. There is hope that stem cell therapy may prove beneficial as it has been increasingly well established that stem cells play an important role in wound healing. For example, artificial skin substitutes have been shown to be more effective when stem cells are incorporated into these membranes. The quality of burn wound healing improves (Leonardi et al., 2012), reducing scar formation and re-establishing the skin appendages (Mansilla et al., 2010; Tamai et al., 2011; Huang and Burd, 2012). The treatment of a chronic static diabetic ulcer has been improved by using the patient's bone marrow (BM) mesenchymal stem cells (MSCs) in combination with autologous skin fibroblasts embedded on a biodegradable collagen membrane (ColadermR) (Vojtassak et al., 2006). BM cells from both embryonic and postnatal sources have been shown to repair genetic defects in collagen synthesis and basement membrane defects thereby promoting skin wound healing (Chino et al., 2008; Tolar et al., 2009; Fujita et al., 2010). Recently, a clinical trial found that allogeneic whole BM transplantation in humans suffering from a blistering skin disorder caused by the lack of Col 7 resulted in the restoration of skin integrity and Col 7 expression in basement membranes (Wagner et al., 2010).

Many basic cellular studies have also emphasized the plastic relationships between skin and BM. Fibroblast-like cells in the dermis having hematopoietic and mesenchymal lineages, are derived from BM, and the number of these cells increases after skin wounding (Fathke et al., 2004; Ishii et al., 2005). Donor cells have replaced some keratinocytges after BM transplantation and have persisted in the epidermis for at least 3 years (Korbling et al., 2002). BM cells contribute to fetal skin development as infusion of green fluorescent protein (GFP) BM cells in utero in mice led to the accumulation of GFP-positive cells in the developing dermis, particularly in association with developing hair follicles (Chino et al., 2008).

These abundant studies document the importance of BM stem cells in wound healing and raise the tantalizing possibility that cellular processes can be harnessed to develop practical therapeutic protocols to treat large full thickness burns and massive soft tissue injuries which demand immediate therapy. The promise of improved wound repair by harnessing stem cells is testified by the existence of ninety clinical trials using MSC-based therapies listed in the NIH registry (Cerqueira et al., 2012).

To avoid the preparation of endogenous stem cells which is expensive and time consuming, we proposed in these studies to mobilize endogenous stem cells pharmacologically with AMD3100 and Tacrolimus. AMD3100 has been shown to drive endogenous stem cells from the BM to the blood stream in animals and man. Tacrolimus in low dosages proved to have synergistic effects, and combination treatment promises a simple, safe, and rapid means of presenting stem cells to injured areas. Here we test this hypothesis in the healing of full thickness skin wounds in mice and rats. Finding this treatment was able to reduce the time for complete healing by 25%, we characterized stem/progenitor cells and related cytokines/growth factors in the wound and substantiated the important role of mobilized CD133+ stem cells in angiogenesis and hair follicle regeneration in wound areas using lineage tracing.

SUMMARY OF THE INVENTION

The present invention is based, at least in part, on the discovery that a stem cell mobilizer and an immunosuppressive agent can be used to promote or improve wound healing in patients. Indeed, the pharmacological amplification of endogenous stem cells, as described in the embodiments, of the present invention, is attractive as it provides a simple, rapid means of presenting stem cells to injured areas.

As described herein, the present inventors hypothesized that mobilization of bone marrow stem cells with AMD 3100 (i.e., plerixafor) in combination with low-dose Tacrolimus will, in certain embodiments, promote re-epithelialization and, in further embodiments, facilitate regeneration of hair follicles resulting in a more rapid restoration of normal skin. To test this hypothesis, we first examined the effects of plerixafor, tacrolimus or dual drugs on wound healing in a mouse model of full-thickness skin excision. Second, we characterized stem/progenitor cells and related cytokines/growth factors in wound areas. Finally, we evaluated the contributions of mobilized CD133+ stem cells to angiogenesis and hair follicle regeneration in wound areas by using lineage tracing.

More specifically, in particular embodiments, low-dose, not high dose Tacrolimus (FK-506) improves wound healing via recruitment of SDF-1 producing macrophages into wound areas. In addition, mobilization of bone marrow stem cells with Plerixafor in combination with low-dose Tacrolimus accelerates wound healing, promote re-epithelialization and facilitate hair follicle regeneration. Indeed, the combination of low-dose Tacrolimus and Plerixafor improved wound healing by promoting both re-epithelialization and differentiation of skin components.

Accordingly, in one aspect, the present invention provides methods and compositions useful for improving wound healing in patients. In one embodiment, a method for improving wound healing in a patient comprises administering to the patient a therapeutically effective amount of a stem cell mobilizer and an immunosuppressive agent. In certain embodiments, the stem cell mobilizer is selected from the group consisting of AMD3100, AMD3465, TG-0054, BKT140, G-CSF, GM-CSF, SDF-1, and SCF. In a specific embodiment, the stem cell mobilizer is a CXCR4 antagonist. In a more specific embodiment, the stem cell mobilizer is AMD3100. In other embodiments, the immunosuppressive agent is selected from the group consisting of Tacrolimus, cyclosporine, Orthoclone OKT3, mycophenolate, and sirolimus. In a specific embodiment, the immunosuppressive agent is Tacrolimus. In particular embodiments, the immunosuppressive agent is administered in a low dose amount. In certain embodiments, the stem cell mobilizer and the immunosuppressive agent are the same compound.

In another embodiment, a method for improving wound healing in a patient comprises administering to the patient a therapeutically effective amount of a stem cell mobilizer and a low dose of an immunosuppressive agent. In a more specific embodiment, a method for improving wound healing in a patient comprises administering to the patient a therapeutically effective amount of AMD3100 and a low dose of Tacrolimus. In an even more specific embodiment, the low dose of Tacrolimus is in the range of about 0.01 mg/kg to about 0.05 mg/kg.

The present invention also provides a method for improving wound healing in a patient comprising administering to the patient a therapeutically effective amount of an agent that mobilizes $CD34^+$ and/or $CD133^+$ stem cells and a low dose of an immunosuppressive agent. In certain embodiments, the agent that mobilizes $CD34^+$ and/or $CD133^+$ stem cells is AMD3100 and the immunosuppressive agent is Tacrolimus.

In another aspect, an agent functions as both the stem cell mobilizer and an immunosuppressive agent. In one embodiment, a method for improving wound healing in a patient comprises administering to the patient a low dose of Tacrolimus in an amount sufficient to mobilize stem cells to the peripheral blood of the recipient. In a specific embodiment, the low dose of Tacrolimus is in the range of about 0.01 mg/kg to about 0.05 mg/kg. In another embodiment, the low dose of Tacrolimus results in a blood concentration range of about 0.1 ng/ml to about 10 ng/ml. In a more specific embodiment, the low dose of Tacrolimus is about 0.01 mg/kg to about 0.05 mg/kg. In another embodiment, the low dose comprises about 0.1 µg to 1 mg/kg.

In certain embodiments, the methods further comprise administering a second agent to mobilize stem cells to the peripheral blood. In one embodiment, the stem cell mobilizer is selected from the group consisting of AMD3100, AMD3465, TG-0054, BKT140, G-CSF, GM-CSF, SDF-1, and SCF. In a specific embodiment, the stem cell mobilizer is a CXCR4 antagonist. In a more specific embodiment, the stem cell mobilizer is AMD3100.

The present invention also provides a method for improving wound healing in a patient comprising administering a low dose of Tacrolimus to the patient in an amount sufficient to mobilize $CD34^+$ and/or $CD133^+$ stem cells to the peripheral blood. In a specific embodiment, the low dose of Tacrolimus is about 0.05 mg/kg to about 0.5 mg/kg (in rodents, which can be converted to a human dosing by one of ordinary skill in the art).

In another embodiment, a method for improving wound healing in a patient comprises administering Tacrolimus at a dose of about 0.01 mg/kg/day to about 0.05 mg/kg/day to the patient, wherein the dosage range is sufficient to mobilize $CD34^+$ and/or $CD133^+$ stem cells to the peripheral blood. In another embodiment, a method for improving wound healing in a patient comprising administering Tacrolimus at a dose of about 0.01 mg/kg to about 0.075 mg/kg to the patient, wherein the dosage range is sufficient to mobilize $CD34^+$ and/or $CD133^+$ stem cells to the peripheral blood. In particular embodiments, the patient is diabetic or suffers from a burn injury.

In certain embodiments, the low dose of Tacrolimus results in a blood concentration of about 0.1 ng/ml to about 10 ng/ml. In other embodiments, any amount below about 0.075 mg/kg/day (oral) or below about 0.01 mg/kg/day (IV) can be administered.

A normal dose of Tacrolimus for immunosuppression is about 0.1 mg/kg/day-0.3 mg/kg/day (oral) and about 0.01 mg/kg/day-0.05 mg/kg/day (IV). In certain embodiments, a low dose of Tacrolimus is about one tenth the normal dose, e.g., about 0.01 mg/kg/day-0.03 mg/kg/day (oral) and about 0.001 mg/kg/day-0.005 mg/kg/day (IV).

The present invention provides a stem cell mobilizer and an immunosuppressive agent for use in a method for improving wound healing in a subject, wherein the stem cell mobilizer and the immunosuppressive agent are administered to the subject in a therapeutically effective amount, and wherein the immunosuppressive agent is administered in a low dose amount as described herein. An agent that mobilizes $CD34^+$ and/or $CD133^+$ stem cells and a low dose of an immunosuppressive agent for use in a method of treating an organ transplant recipient wherein said stem cell mobilizer and said immunosuppressive agent are administered to the recipient in a therapeutically effective amount. The stem cell mobilizer and immunosuppressive agent, wherein the agent that mobilizes $CD34^+$ and/or $CD133^+$ stem cells is AMD3100 and the immunosuppressive agent is Tacrolimus. The stem cell mobilizer and immunosuppressive agent for use according to any of the embodiments described here, wherein the stem cell mobilizer and the immunosuppressive agent are the same compound.

BRIEF DESCRIPTION OF THE FIGURES

FIG. 9. Dual drug treatment stimulates hair follicle neogenesis and reduces scarring in rat skin after wounding. A rat model of full thickness skin excision as described above. (a) Hair follicle regeneration was assessed by H&E (left and middle panels) and Masson's trichrome (right panels) staining at post-wounding day 20. Representative images of n=12 individual skin samples per group are shown: scar outlined with broken lines, and arrowheads point to the neogenic hair follicles within healed scars. Scale bar: 200 µm. (b) Quantification of regenerated follicles within rat healed scars (2 mm) or intact skin. Data represent mean±SEM of n=12 individual samples per group. *p<0.05.

DETAILED DESCRIPTION OF THE INVENTION

Figure 1A:
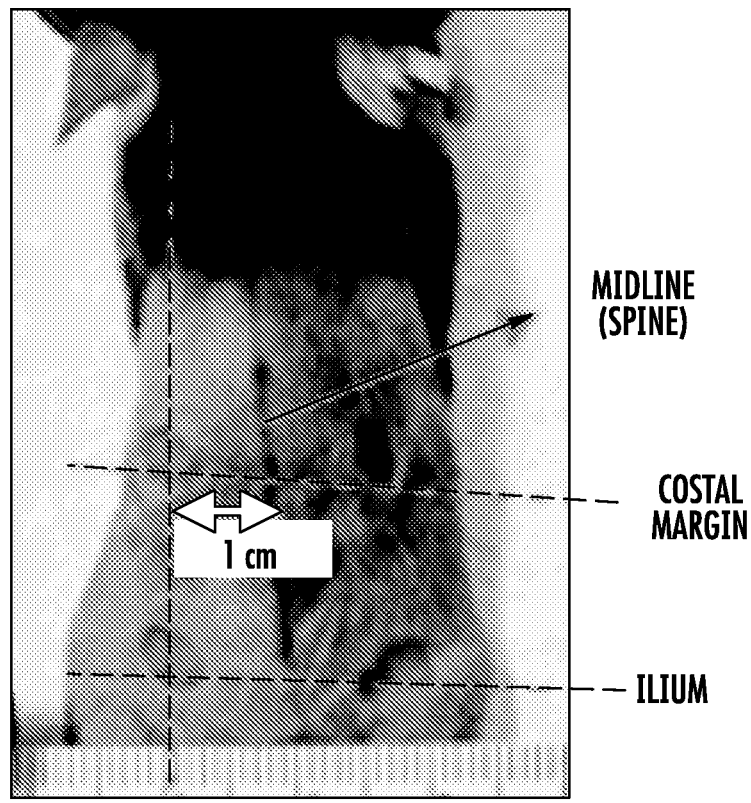
FIG. 1. Accelerated wound healing in mice treated with combination of low-dose Tacrolimus and AMD3100. (a) The model: on day 0, four circular excisional wounds were created in C57BL/6 or CD133+/C-L mice. (b) Wound measurements. Wound areas were determined using Adobe Photoshop software. (c) Early healing. Representative photographs of wounds in mice (n=6) showing striking differences beginning at day 5. (d) Quantitative analysis of wound closure in mice (n=6). *p<0.05. (e) H&E microphotographs of wounds at day 5. Scale bar: 200 µm. (f) The splinted wound model. (g) Macroscopic analysis of skin wound healing in the splinted mice. (h) Quantitative analysis of wound closure in the splinted mice (n=6). *p<0.05. All data represent means±SEM.
Figure 1A:
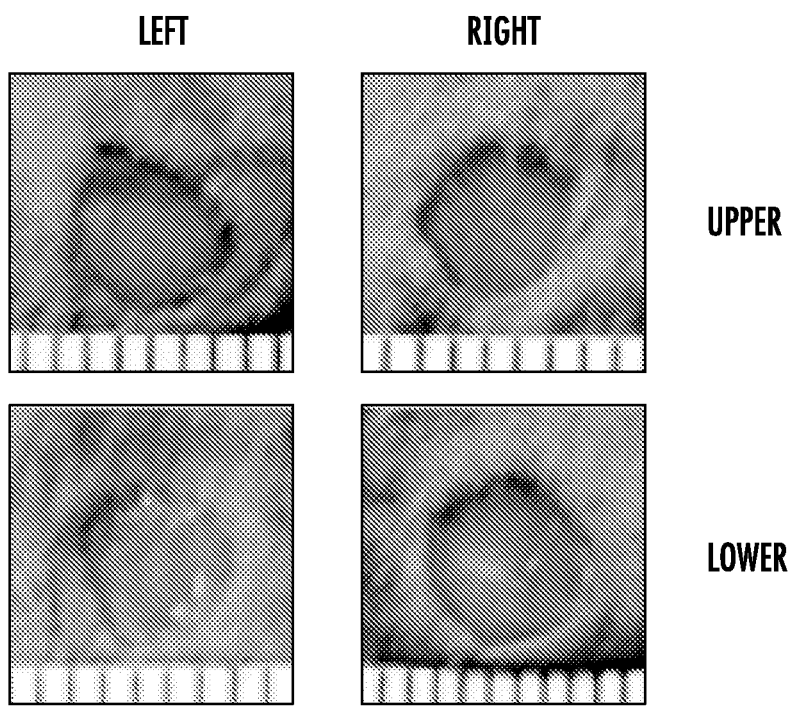

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. DEFINITIONS

"Agent" refers to all materials that may be used as or in pharmaceutical compositions, or that may be compounds such as small synthetic or naturally derived organic compounds, nucleic acids, polypeptides, antibodies, fragments, isoforms, variants, or other materials that may be used independently for such purposes, all in accordance with the present invention.

"Antagonist" refers to an agent that down-regulates (e.g., suppresses or inhibits) at least one bioactivity of a protein. An antagonist may be a compound which inhibits or decreases the interaction between a protein and another molecule, e.g., a target peptide or enzyme substrate. An antagonist may also be a compound that down-regulates expression of a gene or which reduces the amount of expressed protein present.

"Hematopoiesis" refers to the highly orchestrated process of blood cell development and homeostasis. Prenatally, hematopoiesis occurs in the yolk sack, then liver, and eventually the bone marrow. In normal adults it occurs in bone marrow and lymphatic tissues. All blood cells develop from pluripotent stem cells. Pluripotent cells differentiate into stem cells that are committed to three, two or one hematopoietic differentiation pathway. None of these stem cells are morphologically distinguishable, however.

The term "immunosuppressive agent" refers to an agent that inhibits, slows or reverses the activity of the immune system Immunosuppressive agents act by suppressing the function of responding immune cells (including, for example, T cells), directly (e.g., by acting on the immune cell) or indirectly (by acting on other mediating cells).

The terms "stem cells" and "hematopoietic stem cells" are used interchangeably herein. Stem cells are distinguished from other cell types by two important characteristics. First, stem cells are unspecialized cells capable of renewing themselves through cell division, sometimes after long periods of inactivity. Second, under certain physiologic or experimental conditions, stem cells can be induced to become tissue- or organ-specific cells with special functions. In some organs, such as the gut and bone marrow, stem cells regularly divide to repair and replace worn out or damaged tissues. In other organs, however, such as the pancreas and the heart, stem cells only divide under special conditions.

The term "stem cells" can refer to multipotent stem cells that are capable of differentiating into all blood cells including erythrocytes, leukocytes and platelets. For instance, the "hematopoietic stem cells" or "stem cells" as used in the invention are contained not only in bone marrow but also in umbilical cord blood derived cells.

A "stem cell mobilizer," "mobilizer of hematopoietic stem cells or progenitor cells" or "mobilize," (used interchangeably), as described herein, refers to any compound, whether it is a small organic molecule, synthetic or naturally derived, or a polypeptide, such as a growth factor or colony stimulating factor or an active fragment or mimic thereof, a nucleic acid, a carbohydrate, an antibody, or any other agent that acts to enhance the migration of stem cells from the bone marrow into the peripheral blood. A stem cell mobilizer may increase the number of hematopoietic stem cells or hematopoietic progenitor/precursor cells in the peripheral blood, thus allowing for a more accessible source of stem cells for use in wound healing. In particular embodiments, a stem cell mobilizer refers to any agent that mobilizes CD34+ and/or CD133+ stem cells. In other embodiments, a stem cell mobilizer disrupts CXCL12 (SDF-1)-mediated chemoattraction of CXCR4-expressing cells.

A "patient," "subject," or "host," to be treated by the present methods refers to either a human or non-human animal, such as primates, mammals, and vertebrates.

A "small molecule" refers to a composition that has a molecular weight of less than 3 about kilodaltons (kDa), less than about 1.5 kilodaltons, or less than about 1 kilodalton. Small molecules may be nucleic acids, peptides, polypeptides, peptidomimetics, carbohydrates, lipids or other organic (carbon-containing) or inorganic molecules. A "small organic molecule" is an organic compound (or organic compound complexed with an inorganic compound (e.g., metal)) that has a molecular weight of less than about 3 kilodaltons, less than about 1.5 kilodaltons, or less than about 1 kDa.

As used herein, the terms "treatment," "treating," "treat" and the like, refer to obtaining a desired pharmacologic and/or physiologic effect. The terms are also used in the context of the administration of a "therapeutically effective amount" of an agent, e.g., a stem cell mobilizer and/or an immunosuppressive agent. The effect may be prophylactic in terms of completely or partially preventing a particular outcome, disease or symptom thereof and/or may be therapeutic in terms of a partial or complete cure for a disease and/or adverse affect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease. In particular embodiments, the term is used in the context of promoting or improving wound healing in patients.

II. STEM CELL MOBILIZERS

The present invention relates to the treatment of wounds with a stem cell mobilizer in combination with an immunosuppressive agent. Generally, stem cell mobilizers include, but are not limited to, small organic molecules, polypeptides, nucleic acids, and carbohydrates.

In the case of a polypeptide, the stem cell mobilizer may comprise a cytokine, a colony stimulating factor, a protease or a chemokine. More specifically, the cytokine may include, but is not limited to, interleukin-1 (IL-1), interleukin-3 (IL-3), interleukin-6 (IL-6), interleukin-11 (IL-11), interleukin-7 (IL-7), and interleukin-12 (IL12).

In the case of a colony stimulating factor, the stem cell mobilizer may include, but is not limited to, granulocyte colony stimulating factor (G-CSF), granulocyte-macrophage colony stimulating factor (GM-CSF), macrophage colony stimulating factor (M-CSF), stem cell factor, FLT-3 ligand or a combination thereof.

In another embodiment, the protease stem cell mobilizer may include, but is not limited to, metalloproteinase (like MMP2 or MMP9) a serine protease, (like cathepsin G, or elastase) a cysteine protease (like cathepsin K) and a dipeptidyl peptidase-1 (DDP-1 OR CD26).

In yet another embodiment, the chemokine stem cell mobilizer may include, but is not limited to, CXCL12, IL-8, Mip-1α, and Groβ.

In yet another embodiment, the nucleic acid stem cell mobilizer is a DNA or an RNA molecule. In more specific embodiments, the nucleic acid can be a small interfering RNA (siRNA) molecule or an antisense molecule specific for CXCL12.

In the case of a carbohydrate, the stem cell mobilizer can be a sulfated carbohydrate may include, but is not limited to, Fucoidan and sulfated dextran. Fucoidan is a carbohydrate consisting of L-fucose, sulfate and acetate in a molar proportion of 1:1.23:0.36 and can be isolated from the Pacific brown seaweed Fucus evanescens. See Bilan et al., 337(8) CARBOHYDRATE RESEARCH 719-30 (2002). Sulfated dextrans refer to a series of polysaccharides that have variable sulfated patterns. See, e.g. Pomin et al., 15(12) GLYCOBIOLOGY 1376-1385 (2005); Melo et al., 279(2) J. BIOL. CHEM. 20824-20835 (2004); and Farias et al., 275(38) J. BIOL. CHEM. 29299-29307 (2000).

Stem cell mobilizers may further include, but are not limited to, AMD3100; stromal cell-derived factor (SDF-1); SDF-1 analogs (e.g., CTCE-0214 (Chemokine Therapeutics Corp.)); anti-SDF-1 antibodies; cyclophosphamide; stem cell factor (SCF); filgrastim; ancestim; Myeloid Progenitor Inhibitory Factor-1 (MPIF-1) (see U.S. Patent Publication No. 20080274109); and Very Late Antigen (VLA-4) antagonists (e.g., an alpha-4 integrin antagonist, such as an antibody including Natalizumab or Anti-phospho-Integrin α4 (Ser988), clone 6.33 (Upstate Cell Signaling Solutions), or a peptide (e.g., phenylacetyl-leu-asp-phe-D-prolineamide (Cytel Corp., San Diego Calif.))).

In particular embodiments, the stem cell mobilizer comprises a CXCR4 antagonist. In specific embodiments, the CXCR4 antagonist is TG-0054 (TaiGen Biotechnology Co., Ltd. (Taipei, Taiwan)). In other specific embodiments, the CXCR4 antagonist is AMD3465. In yet other embodiments, the CXCR4 antagonist is AMD3100. AMD3100 (1,1'-[1,4-phenylenebis(methylene)]bis-1,4,8,11-tetraazacyclo-tetradecane) is a symmetric bicyclam, prototype non-peptide antagonist of the CXCR4 chemokine receptor. See U.S. Pat. Nos. 6,835,731 and 6,825,351. The term "AMD" or "AMD3100" is used interchangeably with Plerixafor, rINN, USAN, JM3100, and its trade name, Mozobil™. For convenience, the term "Plerixafor" is used throughout to refer to a CXCR4 antagonist.

The present invention also contemplates using mimetics of AMD3100. Mutational substitutions at 16 positions located in TM-III, -IV, -V, -VI, and -VII lining the main ligand-binding pocket of the CXCR4 receptor have identified three acid residues: $Asp^{171}$ (AspIV:20), $Asp^{262}$ (AspVI:23), and $Glu^{288}$ (GluVII:06) as the main interaction points for AMD3100. Molecular modeling suggests that one cyclam ring of AMD3100 interacts with $Asp^{262}$ in TM-IV, whereas the other ring is sandwiched between the carboxylic acid groups of $Asp^{262}$ and $Glu^{288}$ from TM-VI and -VII, respectively. In one study, it was found that introduction of only a Glu at position VII:06 and the removal of a neutralizing Lys residue at position VII:02 resulted in a 1000-fold increase in affinity of AMD3100 to within 10-fold of its affinity in CXCR4. Thus, mimetics, such as for example, peptide or non-peptide antagonists with improved oral bioavailability can be designed to efficiently and selectively block the CXCR4 receptor.

In other embodiments, the stem cell mobilizer is BKT140 (Biokin Therapeutics, Ltd. (Rehovot, Israel). BKT140 (4F-benzoyl-TN14003) binds and inhibits the CXCR4 chomokin receptor with high affinity, showing an $IC_{50}$ of ~1 nmol/L compared with the values obtained with AMD3100. Moreover, BKT140 hinders the cell migration stimulated by CXCL12 within $IC_{50}$ values of 0.5 to 2.5 nmol/L compared with $IC_{50}$ value of 51±17 nmol/L for Plerixafor, suggesting a high mobilization capacity. See Peled et al., 20 CLIN. CANCER RES. 469-79 (2013).

III. IMMUNOSUPPRESSIVE AGENTS

In conjunction with a stem cell mobilizer, immunosuppressive agents can be used to improve wound healing in patients. The term "immunosuppressive agent" refers to an agent that inhibits, slows or reverses the activity of the immune system Immunosuppressive agents act by suppressing the function of responding immune cells (including, for example, T cells), directly (e.g., by acting on the immune cell) or indirectly (by acting on other mediating cells).

A number of immunosuppressive agents can be used to improve wound healing in patients. Such immunosuppressive agents include, but are not limited to, a calcineurin inhibitor (e.g., cyclosporin (CsA) and analogs thereof; ISA (TX) 247, and tacrolimus (FK-506)); azathioprine (AZ); mycophenolate mofetil (MMF); mizoribine (MZ); leflunomide (LEF); adrenocortical steroids (also known as adrenocortical hormones, corticosteroids, or corticoids) such as prednisolon and methylprednisolon; sirolimus (also known as rapamycin); everolimus; FK778; TAFA-93; deoxyspergualin (DSG); and FTY720 (chemical name: 2-amino-2-[2-(4-octylphenyl)ethyl]-1,3-propanediol hydrochloride).

In other embodiments, the immunosuppressive agent can include, but is not limited to, cyclophosphamide; 15-deoxyspergualin (Gusperimus); interferons; sulfasalazine; mimoribine, misoprostol, anti-IL-2 receptor antibodies, thalidomide, anti-tumor necrosis factor antibodies, anti-CD2 antibodies, anti-CD147 antibodies, anti-CD4 antibodies, anti-CD8 antibodies and anti-thymocyte globulin antibodies Immunosuppressive agents also include ORTHOCLONE® (OKT3) (Ortho Biotech, Raritan, N.J.), SANDIMMUNE® ORAL (cyclosporine) (Sandoz Pharmaceuticals, Hanover, N.J.), PROGRAF® (tacrolimus) (Fujisawa Pharmaceuticals, Deerfield, Ill.), CELLCEPT® (mycophenolate) (Roche Pharmaceuticals, Nutley, N.J.) and RAPAMUNE® (sirolimus) (Wyeth, Collegeville, Pa.). Optionally, the immunosuppressive agent is rapamycin, tacrolimus, mycophenolic acid, azathioprine or cyclophosphamide.

Immunosuppressive agents can further include an interleukin-2 α-chain blocker (e.g., basiliximab and daclizumab); an inhibitor of inosine monophosphate dehydrogenase (e.g., mycophenolate mofetil); and an inhibitor of dihydrofolic acid reductase (e.g., methotrexate).

In particular embodiments, the immunosuppressive agent is Tacrolimus. Tacrolimus (also FK-506 or Fujimycin) is an immunosuppressive drug that is mainly used after allogeneic organ transplant to reduce the activity of the patient's immune system and so lower the risk of organ rejection. It reduces interleukin-2 (IL-2) production by T-cells. It is also used in a topical preparation in the treatment of severe atopic dermatitis (eczema), severe refractory uveitis after bone marrow transplants, and the skin condition vitiligo. It is a 23-membered macrolide lactone discovered in 1984 from the fermentation broth of a Japanese soil sample that contained the bacteria Streptomyces tsukubaensis. The drug is sold under the trade names Prograf® given twice daily, Advagraf® a sustained release formulation allowing once daily dosing, and Protopic® the topical formulation. In particular embodiments, a low dose of Tacrolimus is used in combination with a stem cell mobilizer, e.g., plerixafor. Notably, in certain embodiments, a low dose of Tacrolimus can act as a stem cell mobilizer and an immunosuppressive agent. Thus, in such embodiments, a low dose of Tacrolimus can be used to improve wound healing.

IV. PHARMACEUTICAL COMPOSITIONS AND ADMINISTRATION

Accordingly, a pharmaceutical composition of the present invention may comprise an effective amount of a stem cell mobilizer and/or an immunosuppressive agent. The present invention further contemplates the use of an agent that has characteristics of both a stem cell mobilizer and an immunosuppressive agent. For example, Tacrolimus may be used as both a stem cell mobilizer and an immunosuppressive agent. Still further, the present invention contemplates the use of an effective amount of at least one stem cell mobilizer and/or at least one immunosuppressive agent. As used herein, the term "effective," means adequate to accomplish a desired, expected, or intended result. More particularly, an "effective amount" or a "therapeutically effective amount" is used interchangeably and refers to an amount of a stem cell mobilizer and/or an immunosuppressive agent, perhaps in further combination with yet another therapeutic agent, necessary to provide the desired "treatment" (defined herein) or therapeutic effect, e.g., an amount that is effective to prevent, alleviate, treat or ameliorate symptoms of a disease or prolong the survival of the subject being treated. In particular embodiments, the pharmaceutical compositions of the present invention are administered in a therapeutically effective amount to improve wound healing in a patient. As would be appreciated by one of ordinary skill in the art, the exact amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

In certain embodiments, the immunosuppressive agent (e.g., Tacrolimus) is administered in low dose amount. The phrase "low dose" or "low dose amount" of Tacrolimus in the context of the present invention (in combination with a stem cell mobilizer or alone) refers to the use of a particular amount of an immunosuppressive (e.g., Tacrolimus) that is lower than typically used for immunosuppression. In certain embodiments, the low dose is about $1/10$ of the amount used for immunosuppression. In other embodiments, the low dose of Tacrolimus is about $1/2$, about $1/3$, about $1/4$, about $1/5$, about $1/6$, about $1/7$, about $1/8$, or about $1/9$ of the amount used for immunosuppression. In further embodiments, the low dose of Tacrolimus is about 0.9 times, about 0.8 times, about 0.7 times, about 0.6 times, about 0.5 times, about 0.4 times, about 0.3 times, about 0.2 times, about 0.1 times, about 0.09 times, about 0.08 times, about 0.07 times, about 0.06 times, about 0.05 times, about 0.04 times, about 0.03 times, about 0.02 times, about 0.01 times, about 0.009 times, about 0.08 times or about 0.07 times less than the typical amount used for a particular situation (i.e., typical immunosuppression amounts may differ). In specific embodiments, a low dose of an immunosuppressive agent (e.g., Tacrolimus) is about 0.01 mg/kg to about 0.5 mg/kg, more specifically, about 0.01 mg/kg to 0.5 mg/kg, about 0.01 mg/kg to about 0.45 mg/kg, about 0.01 mg/kg to about 0.4 mg/kg, about 0.01 mg/kg to about 0.35 mg/kg, about 0.06 mg/kg to about 0.45 mg/kg, about 0.07 mg/kg to about 0.4 mg/kg, about 0.08 mg/kg to about 0.35 mg/kg, about 0.09 mg/kg to about 0.3 mg/kg, about 0.1 mg/kg to about 0.25 mg/kg, and so on. In a specific embodiment, the low dose of Tacrolimus is about 0.01 mg/kg to 0.074 mg/kg.

A normal dose of Tacrolimus for immunosuppression is about 0.1 mg/kg/day-0.3 mg/kg/day (oral) and about 0.01 mg/kg/day-0.05 mg/kg/day (IV). In certain embodiments, a low dose of Tacrolimus is about one tenth the normal dose, e.g., about 0.01 mg/kg/day-0.03 mg/kg/day (oral) and about 0.001 mg/kg/day-0.005 mg/kg/day (IV). In other embodiments a low dose of Tacrolimus is about $1/5$, $1/6$, $1/7$, $1/8$, $1/9$, $1/10$, $1/11$, $1/12$, $1/13$, $1/14$, or at least $1/15$ of a normal dose used for immunosuppression.

In other embodiments, a low dose of Tacrolimus comprises any amount below about 0.075 mg/kg/day for oral administration. The low dose can comprise any amount below about 0.07, 0.065, 0.06, 0.055, 0.05, 0.045, 0.04, 0.035, 0.03, 0.029, 0.028, 0.027, 0.026, 0.025, 0.024, 0.023, 0.022, 0.021, 0.020, 0.019, 0.018, 0.017, 0.016, 0.05, 0.014, 0.013, 0.012, 0.011, 0.010, 0.009, 0.008, 0.007, 0.006, 0.005, 0.004, 0.003, 0.002, or 0.001 mg/kg/day.

For intravenous administration, a low dose of Tacrolimus comprises any amount below about 0.01 mg/kg/day. The low dose can comprise any amount below about 0.01, 0.009, 0.008, 0.007, 0.006, 0.005, 0.004, 0.003, 0.002, or 0.001 mg/kg/day.

In further embodiments, a low dose of Tacrolimus results in a blood concentration range of about 0.1 ng/ml to about 10 ng/ml. The concentration can be less than about 10 ng/ml, 9 ng/ml, 8 ng/ml, 7 ng/ml, 6 ng/ml, 5 ng/ml, 4 ng/ml, 3 ng/ml, 2 ng/ml, 1 ng/ml, 0.9 ng/ml, 0.8 ng/ml, 0.7 ng/ml, 0.6 ng/ml, 0.5 ng/ml, 0.4 ng/ml, 0.3 ng/ml, 0.2 ng/ml, or 0.1 ng/ml. In a more specific embodiment, the blood tacrolimus concentrations are less than about 5 ng/ml for both oral and IV.

The pharmaceutical compositions of the present invention are in biologically compatible form suitable for administration in vivo for subjects. The pharmaceutical compositions can further comprise a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the stem cell mobilizer and/or the immunosuppressive agent are administered. Such pharmaceutical carriers can be sterile liquids, such as water and oils, including those of petroleum, animal, vegetable or synthetic origin, including but not limited to peanut oil, soybean oil, mineral oil, sesame oil and the like. Water may be a carrier when the pharmaceutical composition is administered orally. Saline and aqueous dextrose may be carriers when the pharmaceutical composition is administered intravenously. Saline solutions and aqueous dextrose and glycerol solutions may be employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried slim milk, glycerol, propylene, glycol, water, ethanol and the like. The pharmaceutical composition may also contain minor amounts of wetting or emulsifying agents, or pH buffering agents.

The pharmaceutical compositions of the present invention can take the form of solutions, suspensions, emulsions, tablets, pills, capsules, powders, sustained-release formulations and the like. The composition can be formulated as a suppository, with traditional binders and carriers such as triglycerides. Oral formulation may include standard carriers such as pharmaceutical grades of mannitol, lactose, starch, magnesium stearate, sodium saccharine, cellulose, magnesium carbonate, etc. In a specific embodiment, a pharmaceutical composition comprises an effective amount of a stem cell mobilizer and/or an immunosuppressive agent together with a suitable amount of a pharmaceutically acceptable carrier so as to provide the form for proper administration to the patient. The formulation should suit the mode of administration.

The pharmaceutical compositions of the present invention may be administered by any particular route of administration including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intraosseous, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, or transdermal means. Most suitable routes are oral administration or injection. In certain embodiments, subcutaneous injection is preferred.

In general, the pharmaceutical compositions comprising a stem cell mobilizer and/or an immunosuppressive agent disclosed herein may be used alone (e.g., a stem cell mobilizer administered with an immunosuppressive agent) or in concert with other therapeutic agents at appropriate dosages defined by routine testing in order to obtain optimal efficacy while minimizing any potential toxicity. The dosage regimen utilizing a pharmaceutical composition of the present invention may be selected in accordance with a variety of factors including type, species, age, weight, sex, medical condition of the patient; the severity of the condition to be treated; the route of administration; the renal and hepatic function of the patient; and the particular pharmaceutical composition employed. A physician of ordinary skill can readily determine and prescribe the effective amount of the pharmaceutical composition (and potentially other agents including therapeutic agents) required to prevent, counter, or arrest the progress of the condition.

Optimal precision in achieving concentrations of the therapeutic regimen (e.g., pharmaceutical compositions comprising a stem cell mobilizer and/or an immunosuppressive agent in combination with another therapeutic agent) within the range that yields maximum efficacy with minimal toxicity may require a regimen based on the kinetics of the pharmaceutical composition's availability to one or more target sites. Distribution, equilibrium, and elimination of a pharmaceutical composition may be considered when determining the optimal concentration for a treatment regimen. The dosages of a pharmaceutical composition disclosed herein may be adjusted when combined to achieve desired effects. On the other hand, dosages of the pharmaceutical compositions and various therapeutic agents may be independently optimized and combined to achieve a synergistic result wherein the pathology is reduced more than it would be if either was used alone.

In particular, toxicity and therapeutic efficacy of a pharmaceutical composition disclosed herein may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effect is the therapeutic index and it may be expressed as the ratio $LD_{50}/ED_{50}$. Pharmaceutical compositions exhibiting large therapeutic indices are preferred except when cytotoxicity of the composition is the activity or therapeutic outcome that is desired. Although pharmaceutical compositions that exhibit toxic side effects may be used, a delivery system can target such compositions to the site of affected tissue in order to minimize potential damage to uninfected cells and, thereby, reduce side effects. Generally, the pharmaceutical compositions of the present invention may be administered in a manner that maximizes efficacy and minimizes toxicity.

Data obtained from cell culture assays and animal studies may be used in formulating a range of dosages for use in humans. The dosages of such compositions lie preferably within a range of circulating concentrations that include the $ED_{50}$ with little or no toxicity. The dosage may vary within this range depending upon the dosage form employed and the route of administration utilized. For any composition used in the methods of the invention, the therapeutically effective dose may be estimated initially from cell culture assays. A dose may be formulated in animal models to achieve a circulating plasma concentration range that includes the $IC_{50}$ (the concentration of the test composition that achieves a half-maximal inhibition of symptoms) as determined in cell culture. Such information may be used to accurately determine useful doses in humans. Levels in plasma may be measured, for example, by high performance liquid chromatography.

Moreover, the dosage administration of the compositions of the present invention may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See WO 00/67776, which is entirely expressly incorporated herein by reference.

More specifically, the pharmaceutical compositions may be administered in a single daily dose, or the total daily dosage may be administered in divided doses of two, three, or four times daily. In the case of oral administration, the daily dosage of the compositions may be varied over a wide range from about 0.1 ng to about 1,000 mg per patient, per day. The range may more particularly be from about 0.001 ng/kg to 10 mg/kg of body weight per day, about 0.1-100 µg, about 1.0-50 µg or about 1.0-20 mg per day for adults (at about 60 kg).

The daily dosage of the pharmaceutical compositions may be varied over a wide range from about 0.1 ng to about 1000 mg per adult human per day. For oral administration, the compositions may be provided in the form of tablets containing from about 0.1 ng to about 1000 mg of the composition or 0.1, 0.2, 0.5, 1.0, 2.0, 5.0, 10.0, 15.0, 100, 150, 200, 250, 300, 350, 400, 450, 500, 550, 600, 650, 700, 800, 900, or 1000 milligrams of the composition for the symptomatic adjustment of the dosage to the patient to be treated. An effective amount of the pharmaceutical composition is ordinarily supplied at a dosage level of from about 0.1 ng/kg to about 20 mg/kg of body weight per day. In one embodiment, the range is from about 0.2 ng/kg to about 10 mg/kg of body weight per day. In another embodiment, the range is from about 0.5 ng/kg to about 10 mg/kg of body weight per day. The pharmaceutical compositions may be administered on a regimen of about 1 to about 10 times per day.

In the case of injections, it is usually convenient to give by an intravenous route in an amount of about 0.0001 µg-30 mg, about 0.01 µg-20 mg or about 0.01-10 mg per day to adults (at about 60 kg). In the case of other animals, the dose calculated for 60 kg may be administered as well. More specifically, in the case of injections, it is usually convenient to give Tacrolimus by a subcutaneous route in an amount of about 0.01 mg/kg to about 0.5 mg/kg of Tacrolimus, more specifically, about 0.01 mg/kg to 0.5 mg/kg, about 0.02 mg/kg to about 0.5 mg/kg, about 0.03 mg/kg to about 0.5 mg/kg, about 0.04 mg/kg to about 0.45 mg/kg, about 0.06 mg/kg to about 0.45 mg/kg, about 0.07 mg/kg to about 0.4 mg/kg, about 0.08 mg/kg to about 0.35 mg/kg, about 0.09 mg/kg to about 0.3 mg/kg, about 0.1 mg/kg to about 0.25 mg/kg, and so on.

Doses of a pharmaceutical composition of the present invention can optionally include 0.0001 µg to 1,000 mg/kg/administration, or 0.001 µg to 100.0 mg/kg/administration, from 0.01 µg to 10 mg/kg/administration, from 0.1 µg to 10 mg/kg/administration, including, but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration or any range, value or fraction thereof.

As a non-limiting example, treatment of subjects can be provided as a one-time or periodic dosage of a composition of the present invention 0.1 ng to 100 mg/kg such as 0.0001, 0.001, 0.01, 0.1 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

In certain embodiments, doses of a pharmaceutical composition of the present invention can optionally include about 0.01 mg/kg to about 0.5 mg/kg of Tacrolimus including, but not limited to, 0.01, 0.02, 0.03, 0.04, 0.05, 0.06, 0.07, 0.08, 0.09, 0.1, 0.2, 0.3, 0.4, and/or 0.5 mg/kg/administration or any range, value or fraction thereof, or to achieve a blood level of about 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20 ng/ml.

Specifically, the pharmaceutical compositions of the present invention may be administered at least once a week over the course of several weeks. In one embodiment, the pharmaceutical compositions are administered at least once a week over several weeks to several months. In another embodiment, the pharmaceutical compositions are administered once a week over four to eight weeks. In yet another embodiment, the pharmaceutical compositions are administered once a week over four weeks.

More specifically, the pharmaceutical compositions may be administered at least once a day for about 2 days, at least once a day for about 3 days, at least once a day for about 4 days, at least once a day for about 5 days, at least once a day for about 6 days, at least once a day for about 7 days, at least once a day for about 8 days, at least once a day for about 9 days, at least once a day for about 10 days, at least once a day for about 11 days, at least once a day for about 12 days, at least once a day for about 13 days, at least once a day for about 14 days, at least once a day for about 15 days, at least once a day for about 16 days, at least once a day for about 17 days, at least once a day for about 18 days, at least once a day for about 19 days, at least once a day for about 20 days, at least once a day for about 21 days, at least once a day for about 22 days, at least once a day for about 23 days, at least once a day for about 24 days, at least once a day for about 25 days, at least once a day for about 26 days, at least once a day for about 27 days, at least once a day for about 28 days, at least once a day for about 29 days, at least once a day for about 30 days, or at least once a day for about 31 days.

Alternatively, the pharmaceutical compositions may be administered about once every day, about once every 2 days, about once every 3 days, about once every 4 days, about once every 5 days, about once every 6 days, about once every 7 days, about once every 8 days, about once every 9 days, about once every 10 days, about once every 11 days, about once every 12 days, about once every 13 days, about once every 14 days, about once every 15 days, about once every 16 days, about once every 17 days, about once every 18 days, about once every 19 days, about once every 20 days, about once every 21 days, about once every 22 days, about once every 23 days, about once every 24 days, about once every 25 days, about once every 26 days, about once every 27 days, about once every 28 days, about once every 29 days, about once every 30 days, or about once every 31 days.

The pharmaceutical compositions of the present invention may alternatively be administered about once every week, about once every 2 weeks, about once every 3 weeks, about once every 4 weeks, about once every 5 weeks, about once every 6 weeks, about once every 7 weeks, about once every 8 weeks, about once every 9 weeks, about once every 10 weeks, about once every 11 weeks, about once every 12 weeks, about once every 13 weeks, about once every 14 weeks, about once every 15 weeks, about once every 16 weeks, about once every 17 weeks, about once every 18 weeks, about once every 19 weeks, about once every 20 weeks.

Alternatively, the pharmaceutical compositions of the present invention may be administered about once every month, about once every 2 months, about once every 3 months, about once every 4 months, about once every 5 months, about once every 6 months, about once every 7 months, about once every 8 months, about once every 9 months, about once every 10 months, about once every 11 months, or about once every 12 months.

Alternatively, the pharmaceutical compositions may be administered at least once a week for about 2 weeks, at least once a week for about 3 weeks, at least once a week for about 4 weeks, at least once a week for about 5 weeks, at least once a week for about 6 weeks, at least once a week for about 7 weeks, at least once a week for about 8 weeks, at least once a week for about 9 weeks, at least once a week for about 10 weeks, at least once a week for about 11 weeks, at least once a week for about 12 weeks, at least once a week for about 13 weeks, at least once a week for about 14 weeks, at least once a week for about 15 weeks, at least once a week for about 16 weeks, at least once a week for about 17 weeks, at least once a week for about 18 weeks, at least once a week for about 19 weeks, or at least once a week for about 20 weeks.

Alternatively the pharmaceutical compositions may be administered at least once a week for about 1 month, at least once a week for about 2 months, at least once a week for about 3 months, at least once a week for about 4 months, at least once a week for about 5 months, at least once a week for about 6 months, at least once a week for about 7 months, at least once a week for about 8 months, at least once a week for about 9 months, at least once a week for about 10 months, at least once a week for about 11 months, or at least once a week for about 12 months.

The pharmaceutical compositions of the present invention (e.g., a stem cell mobilizer and/or an immunosuppressive agent) can be administered simultaneously or sequentially by the same or different routes of administration. The pharmaceutical compositions may further be combined with one or more additional therapeutic agents. The determination of the identity and amount of the pharmaceutical compositions for use in the methods of the present invention can be readily made by ordinarily skilled medical practitioners using standard techniques known in the art. In specific embodiments, a stem cell mobilizer of the present invention can be administered in combination with an effective amount of an immunosuppressive agent. In other specific embodiments, a stem cell mobilizer and an immunosuppressive agent can be administered in combination with an effective amount of another stem cell mobilizer, another immunosuppressive agent, or another therapeutic agent.

In various embodiments, the stem cell mobilizer of the present invention in combination with an immunosuppressive agent (and optionally another stem cell mobilizer, another immunosuppressive agent, or another therapeutic agent) may be administered at about the same time, less than 1 minute apart, less than 2 minutes apart, less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In particular embodiments, two or more therapies are administered within the same patent visit.

In certain embodiments, the stem cell mobilizer of the present invention in combination with an immunosuppressive agent (and optionally another stem cell mobilizer, another immunosuppressive agent, or another therapeutic agent) are cyclically administered. Cycling therapy involves the administration of a first therapy (e.g., the stem cell mobilizer) for a period of time, followed by the administration of a second therapy (e.g., the immunosuppressive agent) for a period of time, optionally, followed by the administration of perhaps a third therapy for a period of time and so forth, and repeating this sequential administration, e.g., the cycle, in order to reduce the development of resistance to one of the therapies, to avoid or reduce the side effects of one of the therapies, and/or to improve the efficacy of the therapies. In certain embodiments, the administration of the combination therapy of the present invention may be repeated and the administrations may be separated by at least 1 day, 2 days, 3 days, 5 days, 10 days, 15 days, 30 days, 45 days, 2 months, 75 days, 3 months, or at least 6 months.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Pharmacologcal Mobilization of Endogenous Stem Cells Significantly Promotes Skin Regeneration after Full-Thickness Excision: The Synergistic Activity of AMD3100 and Tacrolimus Stem cell therapy has shown promise in treating a variety of pathologies including skin wounds, but practical applications remain elusive. Here, we demonstrate that endogenous stem cell mobilization produced by AMD3100 and low-dose Tacrolimus is able to reduce by 25% the time of complete healing of full-thickness wounds created by surgical excision. Equally important, healing was accompanied by reduced scar formation and regeneration of hair follicles. Searching for mechanisms, we found that AMD3100 combined with low-dose Tacrolimus mobilized increased number of lineage-negative c-Kitþ, CD34þ, and CD133 þ stem cells. Low-dose Tacrolimus also increased the number of SDF-1-bearing macrophages in the wound sites amplifying the "pull" of mobilized stem cells into the wound. Lineage tracing demonstrated the critical role of CD133 stem cells in enhanced capillary and hair follicle neogenesis, contributing to more rapid and perfect healing. Our findings offer a significant therapeutic approach to wound healing and tissue regeneration.

Materials and Methods

Animals.

C57BL/6J mice were purchased from the Jackson Laboratory (Bar Harbor, Me.) and designated as wild-type mice in this study. CD133+/C-L mice (Zhu et al., 2009) were obtained from St Jude Children's Research Hospital (Memphis, Tenn.). mT/mG mice were kindly provided by Dr. Steven D. Leach. mT/mG expresses membrane-targeted tdTomato ("mT") prior to Cre excision and membrane-targeted EGFP ("mG") following Cre excision, thereby allowing live visualization and distinction of recombined and non-recombined cells (Muzumdar et al., 2007). When mT/mG mice were crossed with CD133-Cre mice (Zhu et al., 2009), the mG labeling GFP can be generated by inducible CD133-Cre transgenic lines (Zhu et al., 2009). DA (RT1Aa) rats were purchased from Harlan Sprague-Dawley (Indianapolis, Ind., USA). All animals were maintained in the specific pathogen-free facility of the Johns Hopkins Medical Institutions Animals were cared for according to NIH guidelines and under a protocol approved by the Johns Hopkins University Animal Care Committee. Age- and sex-matched mice and rats were used for the experiments. Animals requiring medical attention were provided with appropriate veterinary care or treatment by licensed veterinarians and were excluded from the studies described.

In Vivo Excisional Wound Model.

Figure 7A:
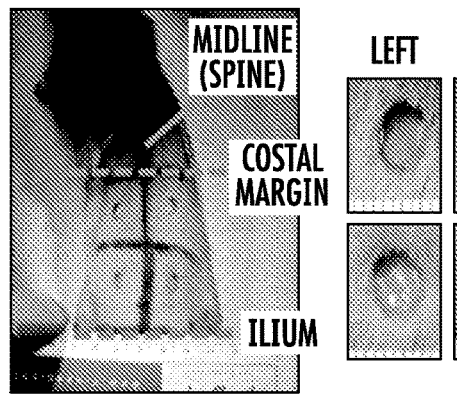
FIG. 7. AMD3100 treatment with low-dose Tacrolimus improved the rate of wound closure in injured rats. (a) Illustrative photographs of the rat model of full-thickness excisional wounds. The wound areas of 5-mm punch biopsies were measured at the indicated time intervals until reaching complete closure. (b) Kinetic analysis of rat skin wound healing. Representative images of n=6 animals per group are showed. (c) Percent wound area at each time point relative to the original wound area was showed. Data represent mean±SEM of n=6 animals per group. *p<0.05 dual treated vs. vehicle treated rats.

Animals aged 8-12 weeks were anesthetized with Isoflurane. The dorsal skin was shaved and cleaned with betadine and 70% ethanol. In mice, the midline and four points 1 cm on each side of the midline were marked by pen. Two points were at the level of the costal margin and two at the iliac crests designating the sites for excision (FIG. 1A). In rats, the four excisional wounds were placed 1 cm to either side of the midline and 1 cm above and below the midpoint between the costal margin and the iliac creasts (FIG. 7a). The sterile disposable biopsy punch (5 mm in diameter; Miltex) was aligned vertically over the center of the mark and punched through the skin and panniculus carnosus by applying pressure and twisting at the same time. The same procedure was repeated, generating four wounds on each animal (Tomlinson and Ferguson, 2003). The animals were house singly after regaining consciousness. For the mouse splinted wound model, one 5 mm excision was made on each side of the midline on the mid back. The donut-shaped, 0.5 mm-thick silicone splints with a diameter two times that of the wound (Grace Bio-Laboratories, Bend, Oreg.) were then centered, sutured and glued (Krazy Glue®; Elmer's Inc., Columbus, Ohio) (FIG. 1F; Galiano et al., 2004).

The animals were injected subcutaneously with AMD3100 (AMD) (1.0 mg kg-1, every two days, Sigma-Aldrich, St Louis, Mo.) or Tacrolimus (T) (0.1 mg kg-1, daily, purchased from Pharmacy at Johns Hopkins hospital). Higher dosages of AMD (5.0 mg kg-1, every two days) or T (1.0 mg kg-1, daily) were administered to wounded mice from day 0 to the day of complete closure to determine dose-responses.

Figure 1B:
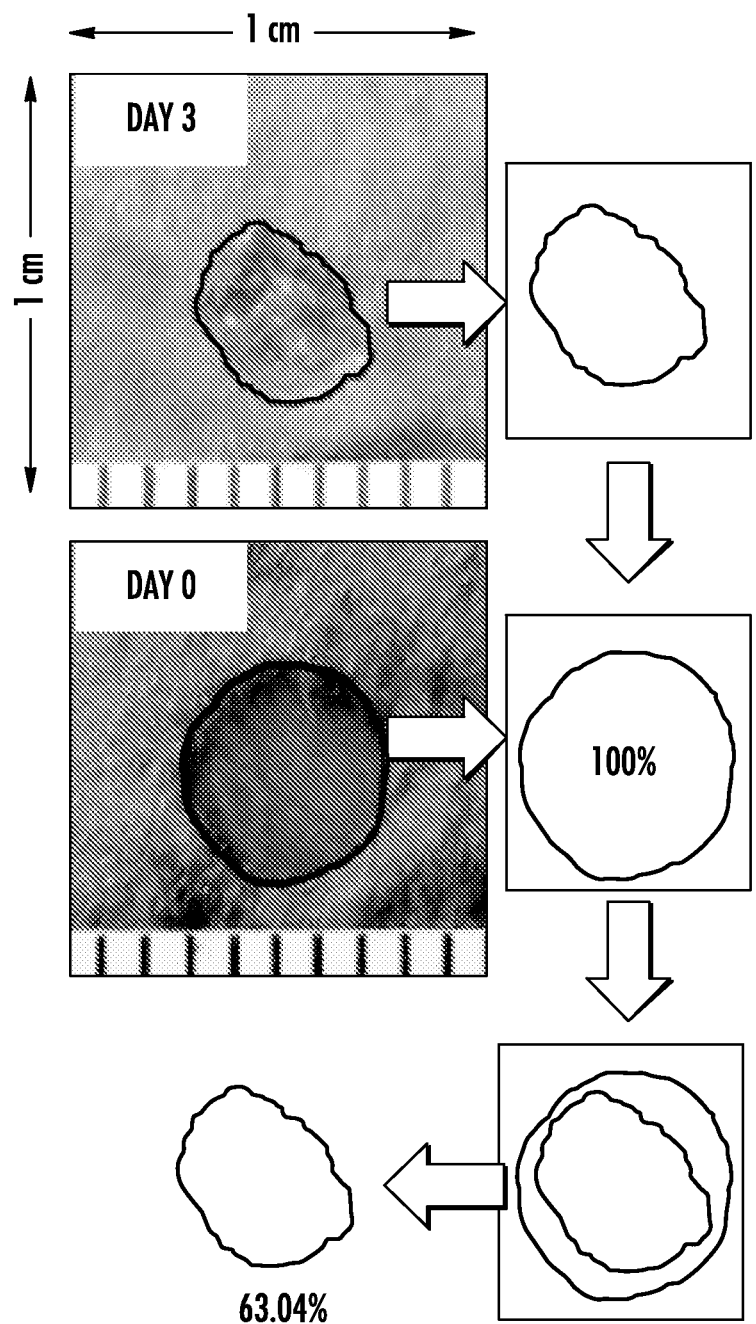

Each wound site was digitally photographed at the indicated time intervals, and wound areas were determined on photographs using Adobe Photoshop (version 7.0; Adobe Systems, San Jose, Calif.). Changes in wound areas over time were expressed as the percentage of the initial wound areas (FIG. 1B).

Inactivation of SDF-1 by Local Intradermal Injection of Anti-SDF-1 Antibodies.

In another series of experiments, following wound creation, ahead of treatment with dual drug therapy (AMD plus low-dose T), 50 µl 15 µg ml-1 (Xu et al., 2013) neutralizing anti-SDF-1 antibodies (MAB310, R&D Systems, Minneapolis, Minn.) in saline were intradermally injected to the two wounds on the right side, whereas the other two wounds on the left side were treated with an equal amount of isotype-matched IgG (MCA1209, AbD Serotec, Raleigh, N.C.) as control. The fluid was injected into the skin bordering the wounds and into the wound beds once daily followed by the combination regimen treatment until wounds were closed. These conducts were paralleled with another negative (vehicle) control group treated with saline alone throughout the entire observation period.

Histology and Microscopy.

Tissues from wound sites were collected at day 3, 5, 7, 9 and 15 after injury.

Lineage Tracing Studies:

The predominant accumulation of CD133+ cells in the wound sites of the dual treated mice (FIG. 3B) prompted the use of an in vivo lineage tracing system to further explore the role of CD133+ stem/progenitor cells in skin regeneration. To activate CreERT2 expressed from the CD133C-L locus, thereby irreversibly activating GFP expression in CD133+ cells and their progeny, 7 days prior to surgery, adult mT/mG; CD133+/C-L-RosaEGFP mice were injected intraperitoneally with 5.0 mg of tamoxifen (Sigma) dissolved in corn oil (FIG. 6a; Muzumdar et al., 2007). Dose and timing of tamoxifen were defined referring to the articles which described the generation of CD133 lineage tracing mice (Nature 2009; 457: 603-607; Genesis 2007; 45:593-605). Animal were sacrificed by CO2 euthanasia at indicated time points and skin samples including and surrounding the wound area were excised, fixed in 2% paraformaldehyde overnight at 4° C., cryo-protected in 30% sucrose overnight at 4° C. and frozen in OCT (optimum cutting temperature). Frozen sections were obtained using a Leica cryostat and slides were washed in PBS for 5 min. The lacZ analysis was performed with commercial β-Galactosidase staining kit (BioVision Inc. Milpitas, Calif.) utilizes X-gal as the substrate. After mounting with 70% glycerol, the sections were observed under a Zeiss microscope for development of blue color. For GFP microscopy, the skin sections were overlaid with mounting medium with DAPI (Vector Laboratories Inc., Burlingame, Calif.) and imaged with a confocal fluorescence microscopy (Carl Zeiss Microscopy, Thornwood, N.Y.). To identify structure of lacZ- and GFP-positive tissues and cells, the same section was sequentially stained with DAPI for GFP fluorescence studies, followed by staining with X-gal and hematoxylin and eosin (H&E) (IHC World, Woodstock, Md.), according to the manufacturer's instructions.

Quantitative Analysis of Hair Follicles:

The number of regenerated hair follicles was quantified in a double-blind fashion. In nonwounded skin, the number of hair follicles in the area from the same location as the wound were counted and compared to experimental groups (FIG. 2A and FIG. 9A; broken lines indicated wound margin). Masson's trichrome (commercial kit from Polysciences, Inc. Warrington, Pa.) was used to detect collagen fibers (blue color).

Immunofluorescence Staining:

For the immunofluorescence staining, frozen sections were fixed with acetone (−20° C.) for 10 min and dried for 1 h at room temperature. PBS containing 1% BSA and 5% normal donkey serum was used to block nonspecific background. Sections were incubated for 1.5 h at room temperature with primary antibodies included: rabbit polyclonal antibody specific for CD133 (1:100, ab19898, Abcam, Cambridge, Mass.), rabbit polyclonal antibody specific for c-Kit (1:100, sc-168, Santa Cruz Biotechnology, Santa Cruz, Calif.), goat polyclonal antibody specific for CD34 (1:100, AF4117, R&D Systems, Minneapolis, Minn.), mouse monoclonal antibody specific for SDF-1 (1:100, MAB310, R&D Systems), FITC-conjugated rat monoclonal antibody specific for F4/80 (1:100, 11-4801, eBioscience, San Diego, Calif.), mouse monoclonal antibody specific for α-SMA (1:100, ab7817, Abcam), rat monoclonal antibody specific for CD31 (1:100, 14-0311, eBioscience) or rabbit polyclonal antibody specific for HGF (1:100, sc-7949, Santa Cruz), or the combinations of two of them for double fluorescence staining. After being rinsed with PBS, the sections were further incubated for 1 h at room temperature with the secondary antibodies of Cy3 donkey anti-rabbit IgG (1:200, 711-166-152, Jackson ImmunoResearch, West Grove, Pa.), Cy3 donkey anti-goat IgG (1:200, 705-166-147, Jackson ImmunoResearch), Cy3 donkey anti-mouse IgG (1:200, 715-615-151, Jackson ImmunoResearch), FITC donkey anti-mouse IgG (1:200, 715-096-150, Jackson ImmunoResearch) or FITC donkey anti-rat IgG (1:200, 712-097-003, Jackson ImmunoResearch), or the combinations of two with different colors (Cy3 and FITC) of them for double fluorescence staining. Cell nuclei were stained blue with DAPI. Tissue sections were analyzed by confocal microscopy (Carl Zeiss Microscopy, Thornwood, N.Y.).

Flow Cytometry.

Peripheral blood was drawn before sacrifice by intracardiac puncture. Red cells were lysed with Red Blood Cell Lysing Buffer Hybri-Max™ (sigma). The residual cells were washed and suspensions (1×106) were analyzed for expression of lineage negative c-Kit+, CD34+ and CD133+ stem cell markers. All antibodies used were from commercial sources, primary antibodies included: CD133 (1:100, ab19898, Abcam), CD34 (1:100, AF4117, R&D Systems), c-Kit (1:100, 14-1171, eBioscience), mouse hematopoietic lineage panel (eBioscience) included biotin-conjugated CD3 (1:100, 13-0031), CD45R/B220 (1:100, 13-0452), CD11b (1:100, 13-0112), TER-119 (1:100, 13-5921) and Ly-6G (1:200, 13-5931); secondary antibodies included: FITC anti rat IgG (1:200, 712-096-150, Jackson ImmunoResearch), PE anti rabbit IgG (1:200, 12-4739, eBioscience), APC anti goat IgG (1:200, 705-136-147, Jackson ImmunoResearch) and streptavidin-PerCP (1:200, 554064, BD Pharmingen). Nonspecific antibody binding was blocked with normal donkey serum (Sigma) for 30 min. Cells were incubated with primary antibodies followed by secondary antibodies for 30 min at 4° C., and the positive cells were counted by flow cytometry (fluorescence activated cell sorting [FACS]) using CELLQuest software (Becton-Dickinson, Bedford, Mass.).

Semiquantitative Reverse Transcription Polymerase Chain Reaction Analysis.

Skin specimens were kept frozen at −80° C. until homogenized for RNA extraction using the TRIzol Reagent (Invitrogen, Carlsbad, Calif., USA). First strand cDNA synthesis was then performed on 5 mg of total RNA using the superscript first-strand synthesis system for reverse transcription polymerase chain reaction (RT-PCR; Invitrogen) according to the manufacturer's instructions. The PCR contained 1 μL of deoxynucleoside triphosphate mix (10 mM each dNTP), 1 μL of 10 μM each primer, 0.4 μL (5 IU μL-1) of Platinum Taq polymerase (Invitrogen), 1.5 μL of 50 mM MgCl2 and 2 μL total DNA as template in a 50 μL reaction solution. Thermal cycling was started with one cycle at 94° C. for 4 min. This was followed by 25-35 cycles at 94° C. for 30 s, 59° C. for 30 s, 72° C. for 30 s and 72° C. for final extension for 10 min. PCR products were electrophoresed on 1.2% agarose gels and visualized with GelStar® Stain (Lonza Rockland Inc., Rockland, Me.). The following primers for mouse samples were used: SDF-1 (GenBank accession no. NM_021704.3): 5'-GACGGTAAACCAGTCAGCCT-3' (forward) (SEQ ID NO:1) and 5'-CACACTTGTCTGTTGTTGTTCTTC-3' (reverse) (SEQ ID NO:2); CD133 (NM_008935.2): 5'-TCCAGCAAACAAGCAACAAG-3' (forward) (SEQ ID NO:3) and 5'-CCTATGCCGAACCAGAACA-3' (reverse) (SEQ ID NO:4); VEGF (NM_001025250.3): 5'-CACTGGACCCTGGCTTTACT-3' (forward) (SEQ ID NO:5) and 5'-GGTGATGTTGCTCTCTGACG-3' (reverse) (SEQ ID NO:6); b-FGF (NM_008006.2): 5'-CAAGG-GAGTGTGTGCCAA-3' (forward) (SEQ ID NO:7) and 5'-TGCCCAGTTCGTTTCAGT-3' (reverse) (SEQ ID NO:8); HGF (NM_010427.4): 5'-ATGAGAGAGGCGAG-GAGAAG-3' (forward) (SEQ ID NO:9) and 5'-GTAGCCCCAGCCGTAAATA-3' (reverse) (SEQ ID NO:10); β-actin (NM_007393.3): 5'-TGGCAC-CACACCTTCTACAAT-3' (forward) (SEQ ID NO:11) and 5'-ACCAGAGGCATACAGGGACA-3' (reverse) (SEQ ID NO:12). The expression levels of target mRNA were quantified by densitometry and normalized with the corresponding internal control.

Statistics.

Continuous variables were presented as the mean±SEM. Dichotomous variables were presented as both number and percentage values. Power analysis was conducted using preliminary data sets for all analyses presented to determine sample sizes necessary for adequate statistical power. Mice and rats were assigned at random to treatment groups for all animal studies. Analyses of wound closure and hair follicle regeneration were performed in a blinded manner. All inclusion/exclusion criteria for animal studies or sample analysis were preestablished. Data of flow cytometry, RT-PCR and de novo follicle counts were analyzed using the Student's t-test (two-tailed), with dichotomous variables analyzed by the Fisher's exact test (two-tailed). Oneway ANOVA with Newman-Keuls test was used for the kinetic analysis of skin wound closure among groups. For each figure, appropriate statistical tests were selected based on the population distribution of data and the number of comparisons (individual or multiple). All the data meet the assumptions of the statistical tests used. There is an estimate of variation within each group of data. The variance between the groups is similar. All analyses were performed using SPSS® (SPSS, Chicago, Ill., USA). The p<0.05 was considered significant.

Results

Example 1

AMD3100 Plus Low-Dose Tacrolimus Accelerated Wound Healing after Full-Thickness Skin Excision Four full-thickness wounds were generated by 5-mm diameter circular excisions on the shaved back of a wild-type C57/B6 mouse (FIG. 1A). Each wound site was photographed digitally at the indicated time intervals, and wound areas were calculated using Adobe Photoshop software. Changes in wound areas over time were expressed as the percentage of the initial wound areas (FIG. 1b). Wounded mice were divided randomly into four experimental groups and received subcutaneous injections of saline or drugs immediately after wounding until complete healing: 1) Control group treated with saline, 2) Tacrolimus group treated daily with low-dose (0.1 mg kg-1), 3) AMD3100 group treated every other day (1.0 mg kg-1) and 4) Combination group given low dose Tacrolimus and AMD3100. All wound evaluations were double blinded.

Figure 1C:
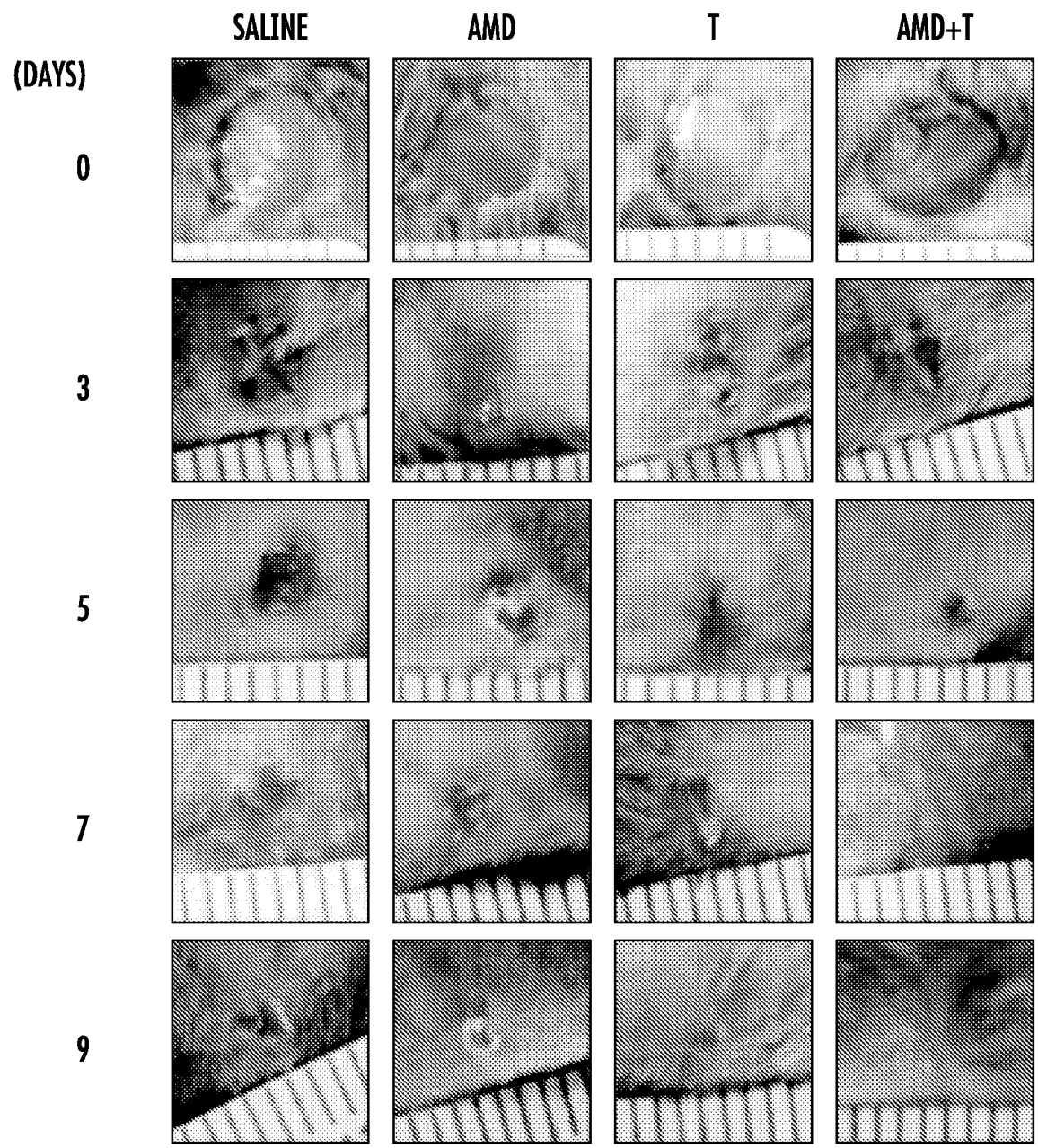
Figure 1D:
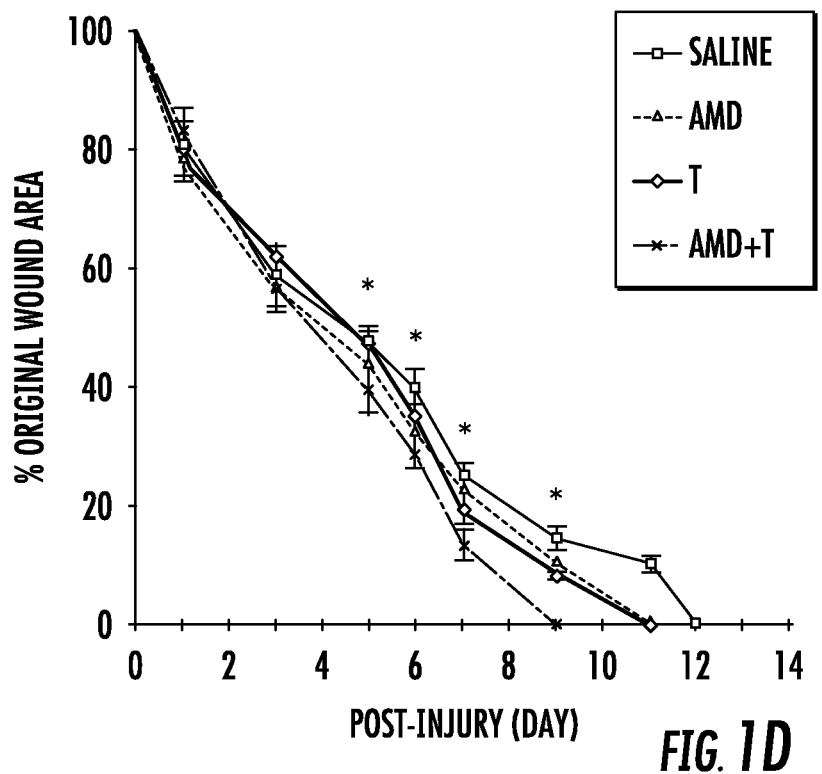
Figure 7B:
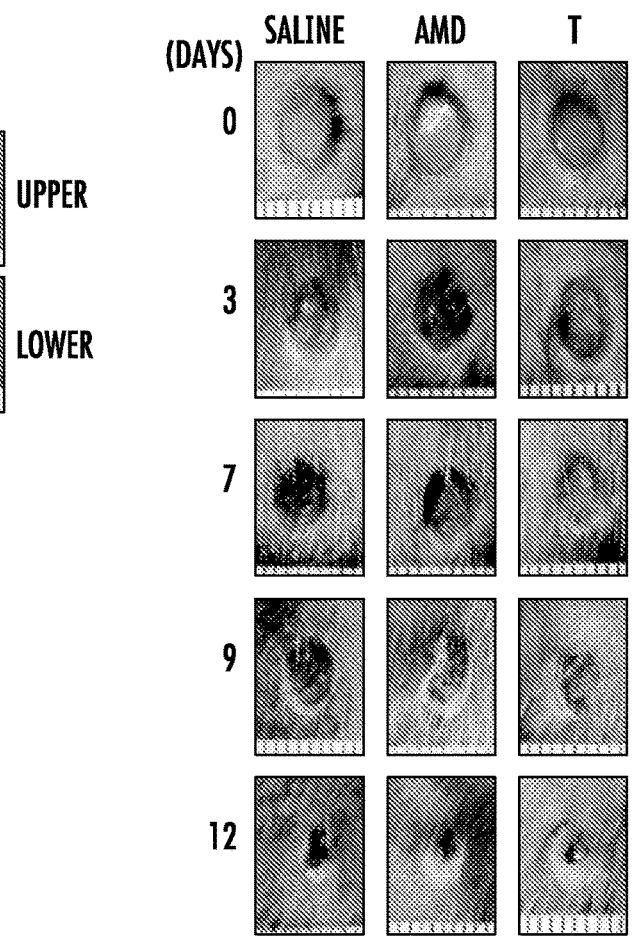
Figure 7C:
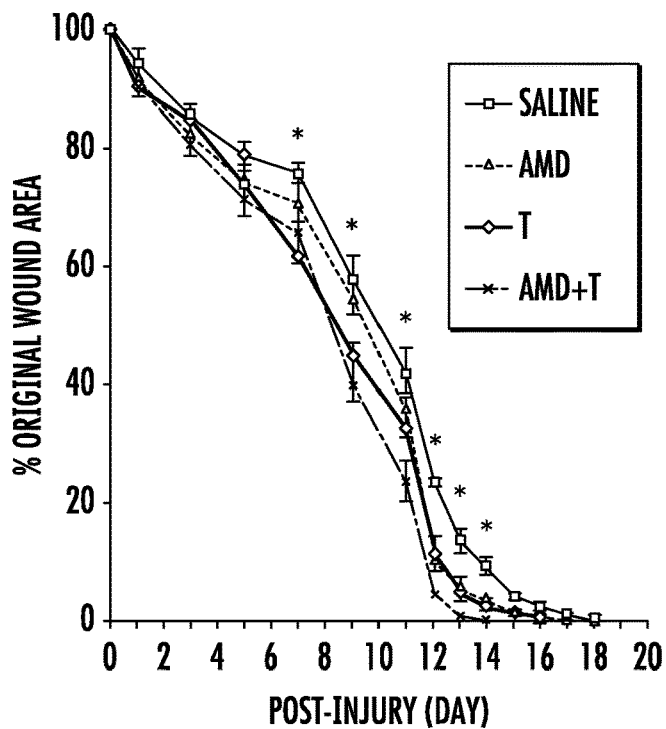

Wounds reached complete closure on day 12 after surgery in group 1 (n=6) (FIGS. 1c and d), which is consistent with the known healing kinetics in this established model (Shinozaki et al., 2009; Mack et al., 2012). The 6 animals treated with Tacrolimus or AMD3100 alone exhibited significantly but only moderately faster healing compared to the saline control group (FIG. 1d) as wounds reached complete closure at day 11. The healing time was reduced to nine days or by 25% in the group 4 mice treated with AMD3100 plus low-dose Tacrolimus. Digital images showed that treatment with dual drug therapy had significant effects reducing the size of the skin defect as soon as day 5 (FIG. 1d), which was the start of the re-epithelialization phase of wound healing. Macroscopically, minimal ulceration and early epithelial ingrowth were observed at the skin boarders on post-wounding day 5 in the dual drug-treated group while wounds in the other three groups showed little if any epithelialization and continued ulceration (FIGS. 1c and h). We repeated these studies in rats and found that rats receiving dual drug therapy also had the equivalent effect significantly reducing the time for complete healing from 18 to 13 days or 28% (FIG. 7).

Figure 1E:
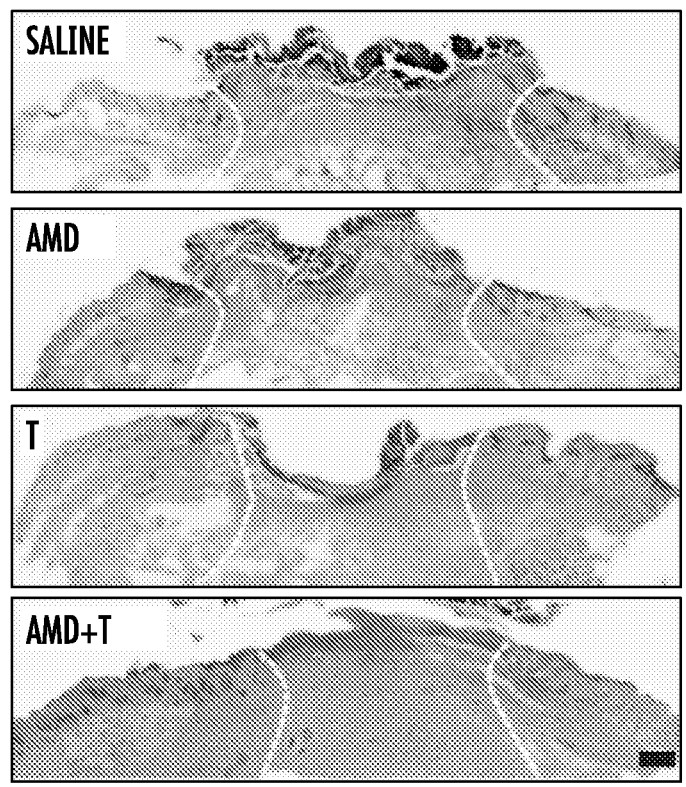
Figure 1F:
Figure 1F:
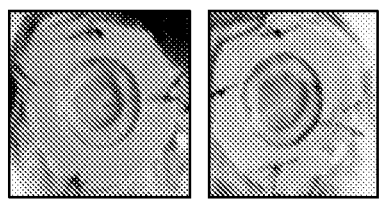
Figure 1G:
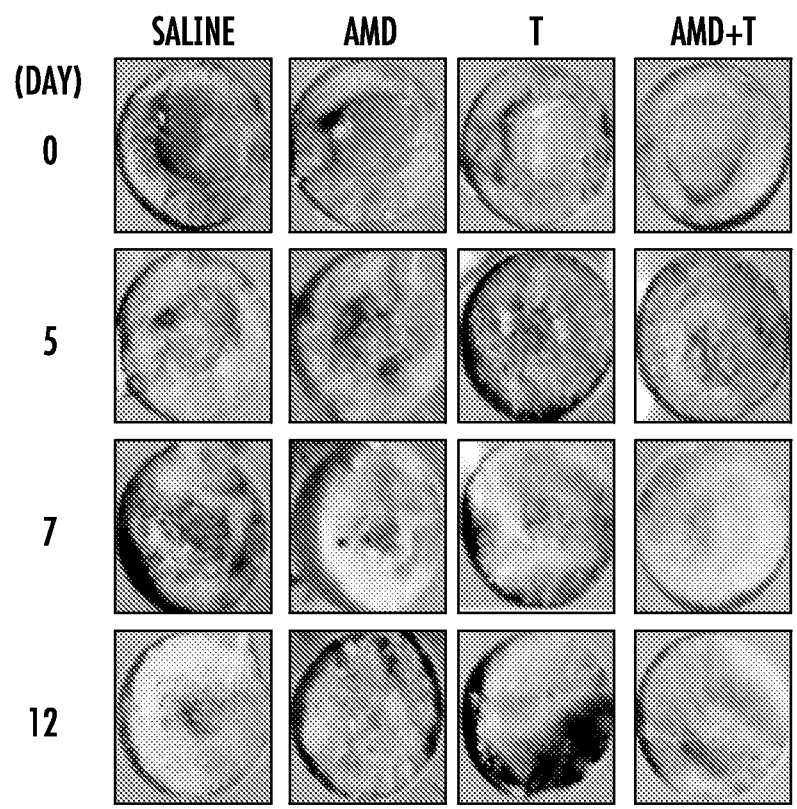
Figure 1H:
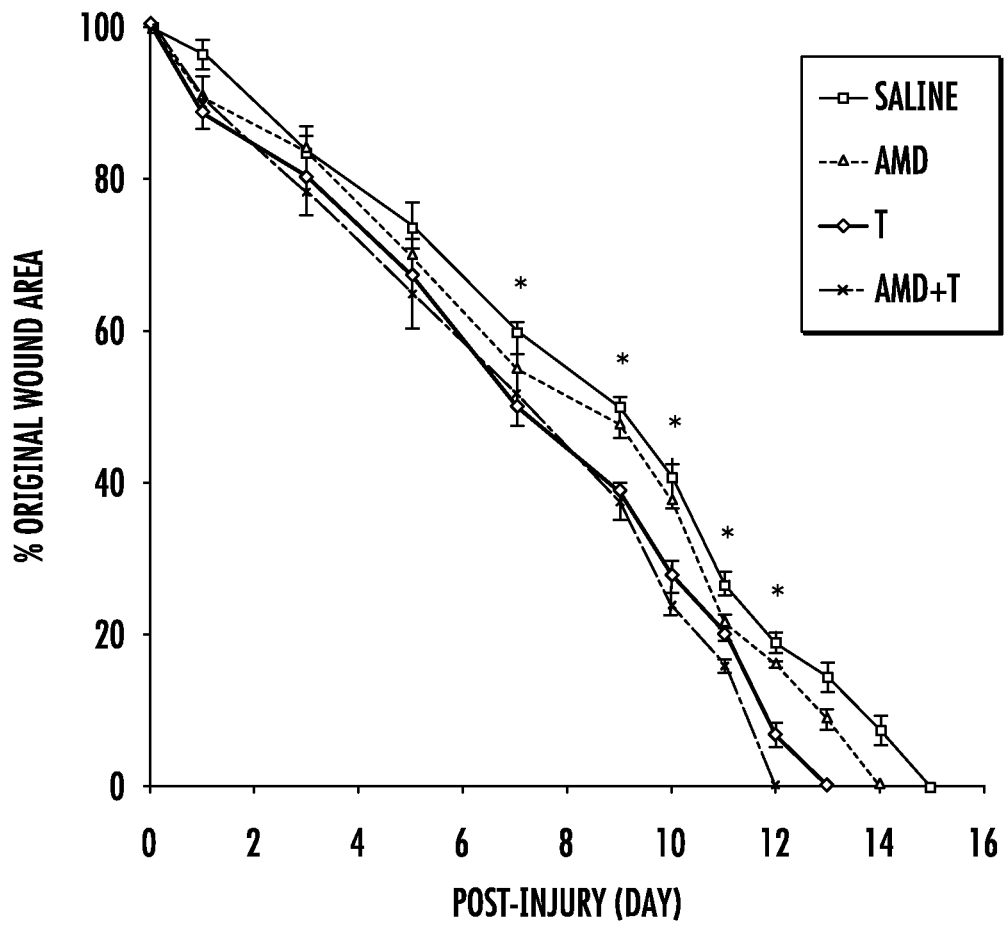
Figure 8A:
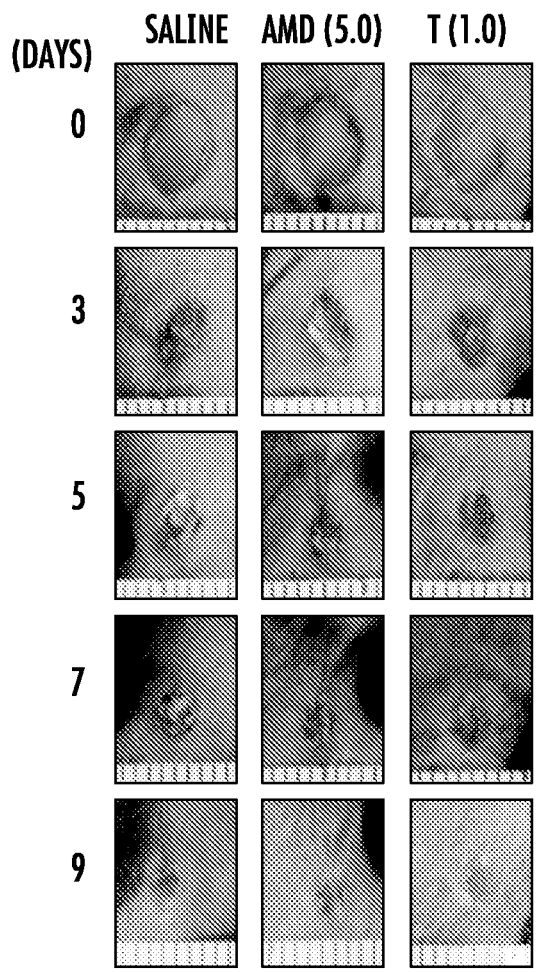
FIG. 8. Effects of Tacrolimus and AMD3100 in high doses on mouse skin wound healing. (a) Kinetic analysis of skin excisional wound healing. Wound sites were photographed at the time indicated. Representative photographs of n=3 or 4 animals per group. (b) Changes in percentage of wound area at each time point in comparison to the original wound area. Data represent mean±SEM of n=3 or 4 animals per group. Quantitative evaluation failed to demonstrate significant difference of wound closure in the mice treated with Tacrolimus (1.0 mg kg-1) or AMD3100 (5.0 mg kg-1) as compared with that in saline treated mice.
Figure 8B:
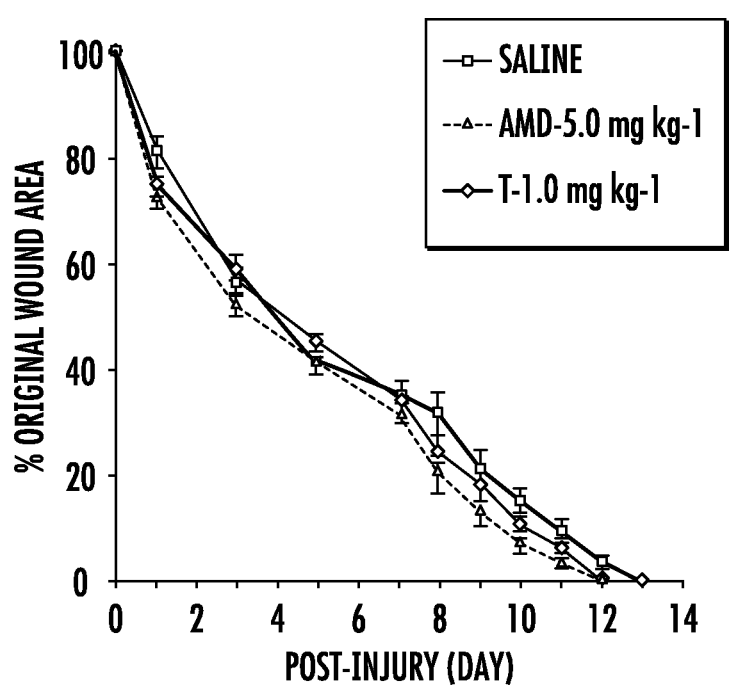

Mouse skin is mobile, and contraction accounts for a large part of wound closure. To deter this mechanism, we performed the excisional wound splinting model, where a splinting ring is bonded tightly to the skin around the wound (FIG. 1e). The wound therefore heals through granulation and re-epithelialization, a process similar to the healing of most human skin defects. We found that wound repair was accelerated in the splinted wounds treated with low dose Tacrolimus or AMD3100 monotherapy compared to the control (saline) group while the most accelerated healing was found in animals receiving dual treatment (FIGS. 1f and g). Thus the therapeutic effects of AMD3100 plus low-dose Tacrolimus were primarily on skin wound epithelialization. Other groups of mice were treated with high-dose AMD3100 (5.0 mg kg-1) or Tacrolimus (1.0 mg kg-1) and we found that high-dose Tacrolimus impeded skin wound healing whereas increased dosage of AMD3100 showed no significant difference (FIG. 8).

Example 2

AMD3100 Plus Low-Dose Tacrolimus Ameliorated Scar Formation and Promoted Hair Follicle Regeneration Dermal wound repair commences with the arrest of hemorrhage followed by an inflammatory response, formation of granulation tissue within the wound space, fibrosis, and re-epithelization of the wound, culminating in the production of a scar.

Figure 2A:
FIG. 2. Increased hair follicle regeneration and diminished scarring in healed skin of mice treated with dual drug therapy. (a) Representative macroscopic appearance of reepithelialized wounds (day 15). (b) Representative microscopic H&E-stained sections from the middle of scars show new hair follicles within healed wounds. The scarred area is outlined by broken lines. Two vertical dotted lines help to demarcate the regions with the same length as that of the healed scar area in saline-treated group. Scale bar: 200 µm. (c) Adjacent sections stained with Masson's trichrome. (d) Representative photographs of dual drug-treated animals at 15 days postwounding showing hair growth in the reepithelialized wound. (e) Quantification of follicles within the healed scars (2 mm) Data represent mean±SEM (n=9). *p<0.01.
Figure 2B:
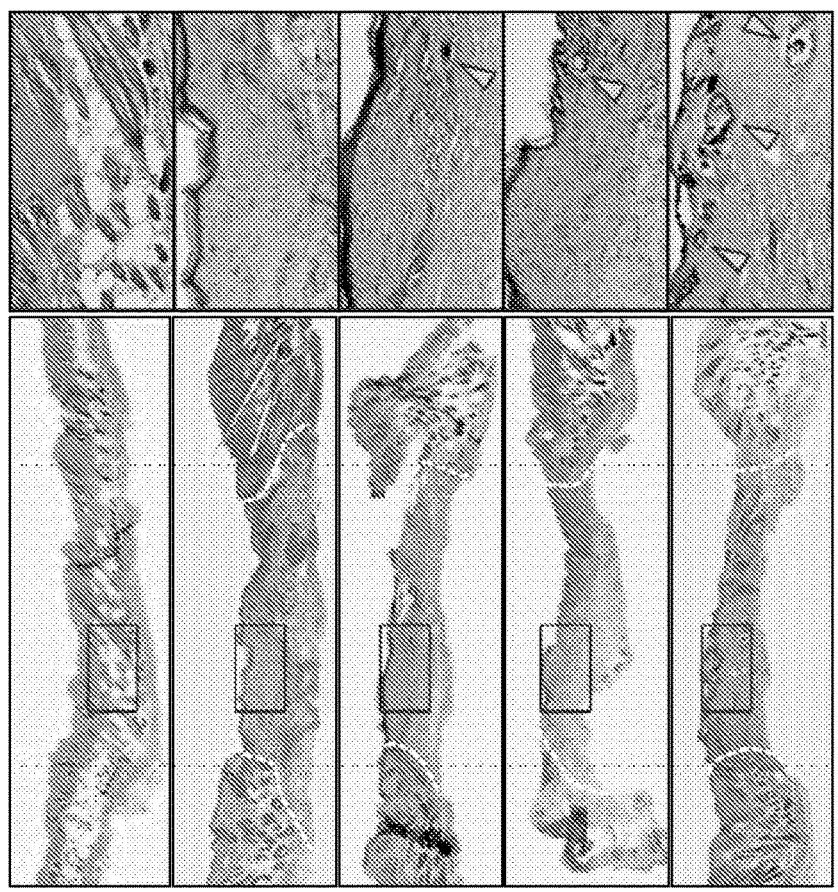
Figure 2C:
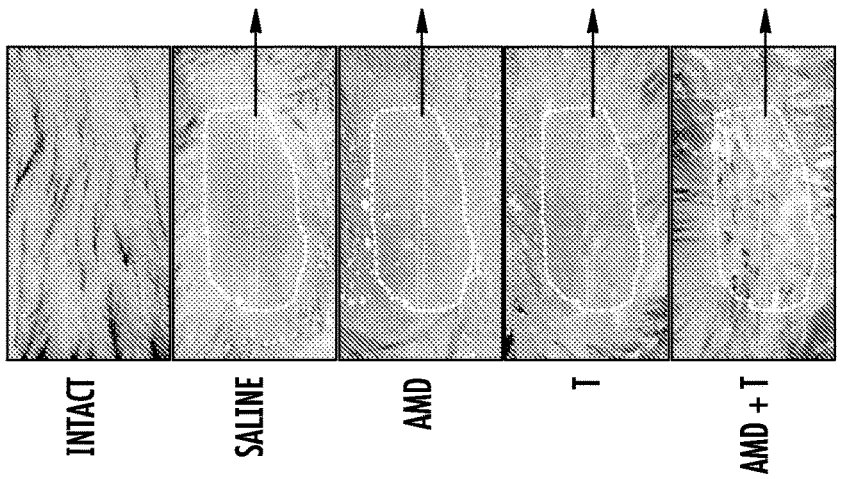
Figure 2E:
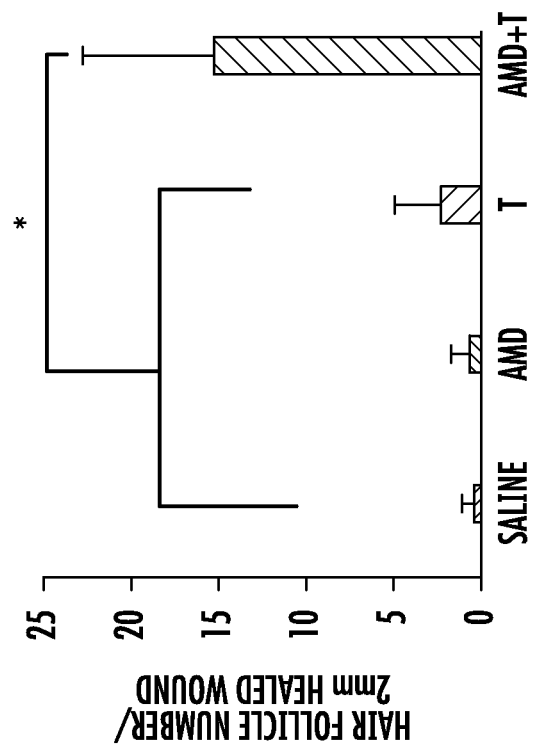
Figure 2D:
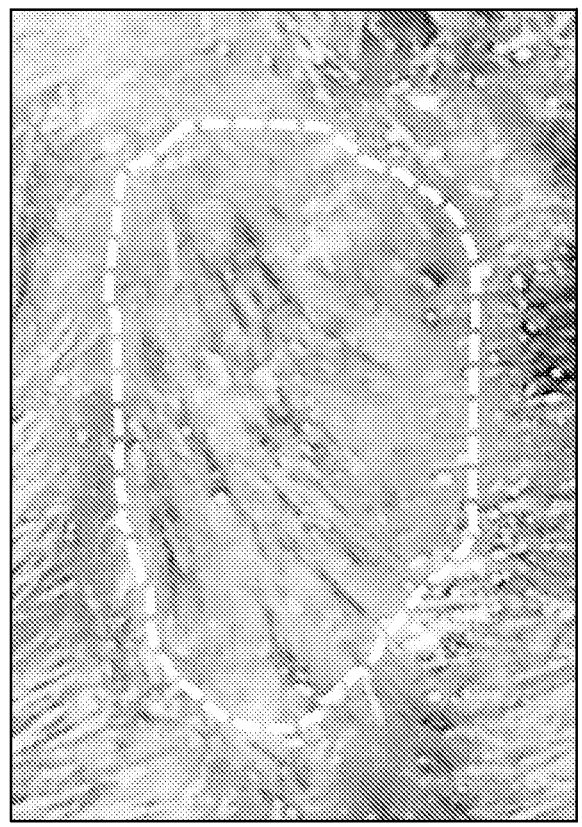

Histologically, the re-epithelialized wound in the control groups on day 15 showed a disorganized epidermis, with blurring of the boundary between the epidermis and the dermis (FIG. 2b). There were few hair follicles in the group 1, 2 and 3 mice and collagen was abundant and disorganized (FIG. 2c), which is in agreement with the results of published studies (Devine et al., 2004). By contrast, the dual drug treated animals had a thin and well organized epidermis with well-formed hair follicles and much better organized collagen (FIGS. 2b and c; lower panels). The most striking finding was that hair appeared only in the reepithelialized wound in the dual drug treated animals after 15 days (FIGS. 2a and d). Not surprisingly, the number of hair follicles in the tissue sections of re-epithelialized wound was significantly higher in the dual drug treated animals compared to the control groups (FIG. 2e). We found that dual drug treatment also stimulated hair follicle neogenesis and reduced scarring in rats (FIG. 9). Thus the combination of low-dose Tacrolimus and AMD3100 improved wound healing by promoting both re-epithelialization and differentiation of skin components.

Example 3

Figure 3A:
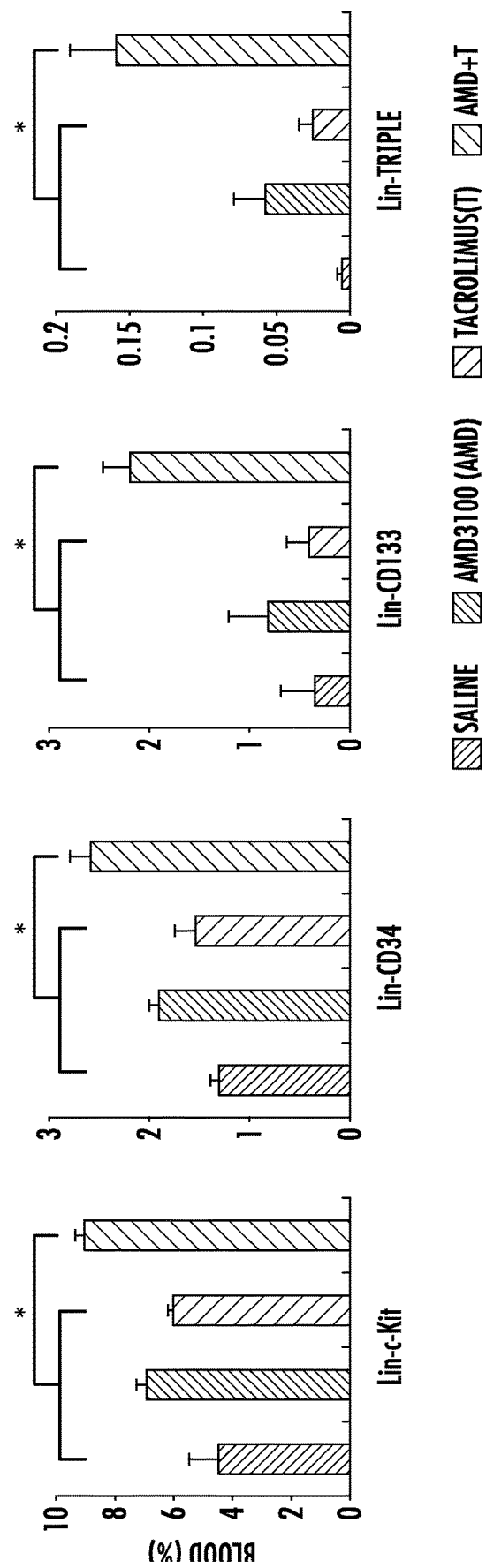
FIG. 3. Recruitment of BM stem cells with dual drug therapy. (a) Quantitative analysis of Lineage negative (Lin−) c-Kit+, CD34+ and CD133+ cells in peripheral blood by flow cytometry at 5 days after injury. Data represent mean±SEM (n=3). *p<0.05. (b) Immunofluorescence staining for stem cell markers c-Kit, CD34 and CD133 and endothelial cells marker CD31 in tissue sections from wounded mice at 5 days after injury. Boxed areas demonstrate at higher magnification that the mice receiving dual drug treatment had a tubular arrangement of CD133 cells which co-stained for CD31. Cell nuclei were stained blue with DAPI. Representative photographs of n=3 individual injured skin samples per group. epi, epidermis; we, wound edge. Scale bar: 200 µm.
Figure 3B:
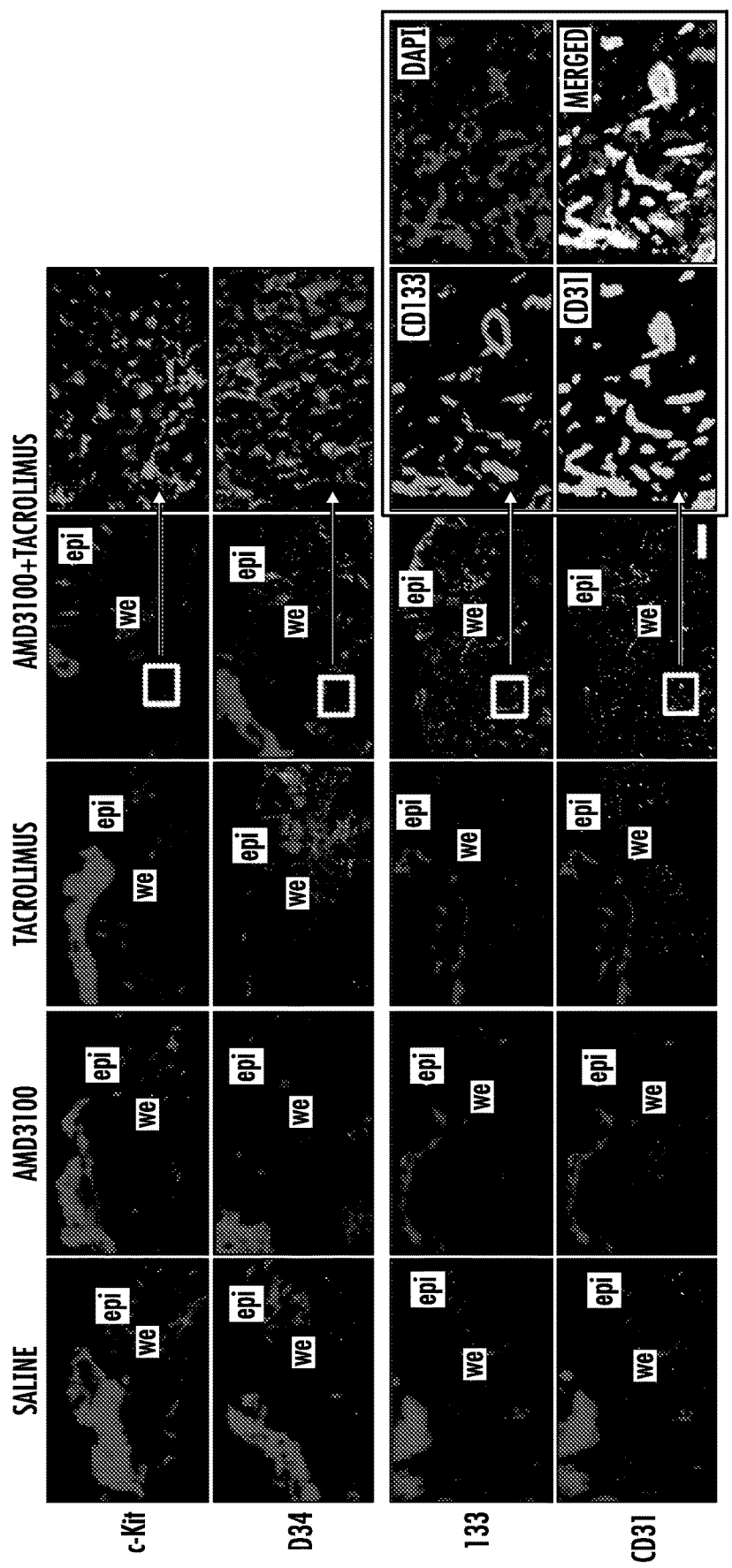

AMD3100 and Low-Dose Tacrolimus Synergistically Mobilized Lineage Negative (Lin−) c-Kit+ CD34+ CD133+ Stem Cells Whereas Low-Dose Tacrolimus Increased the Number of SDF-1 Producing Macrophages We performed flow cytometry on blood samples to determine the stem cell constituents mobilized by treatment with Plerixafor and Tacrolimus. The numbers of Lin−, c-Kit, CD34+, CD133+ cells and Lin-Triple positive (c-Kit+ CD34+ CD133+) cells were significantly greater in peripheral blood (FIG. 3a) in the animals receiving combination drug treatment at 5 days post-injury Immunofluorescence staining of wound tissue sections showed that the number of CD133+ was increased by combination treatment as were c-Kit+ and CD34+ cells (FIG. 3b). These cells were found particularly in newly formed granulation tissues of the wounds. Interestingly, at this 5 day time point, many CD133+ cells co-stained with CD31, a marker of endothelial cells (FIG. 3b; right panels).

Figure 4C:
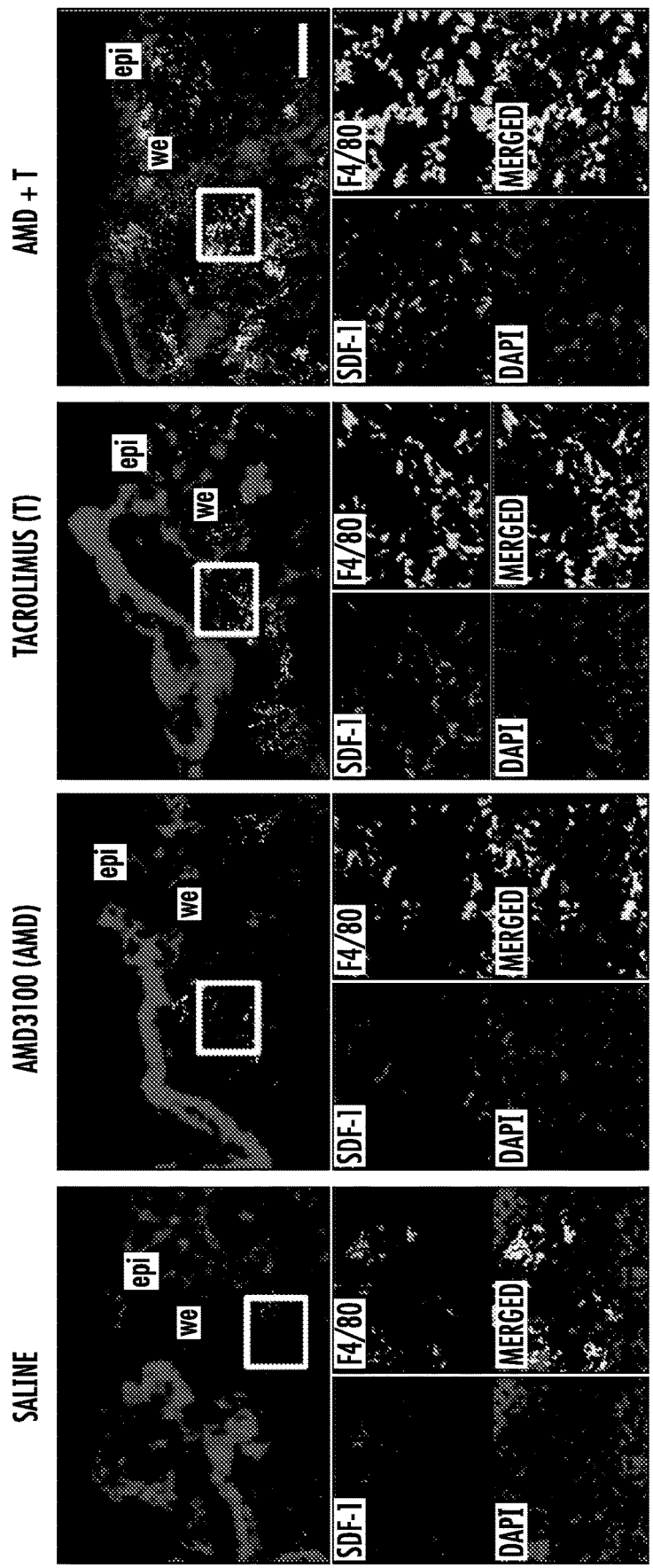
FIG. 4. Increased expression of SDF-1 and CD133 in skin wounds of the mice treated with dual drug therapy. Semi-quantitative RT-PCR analysis of the granulation tissues in wounded skin at 5 days post-injury. (a) The mRNA expression of the attractor molecule SDF-1 was significantly increased in the low-dose Tacrolimus treatment group, and further elevated in the dual treatment group. (b) The stem cell marker CD133 mRNA level was also significantly higher in wounds in the dual treatment group, paralleling SDF-1 gene expression. All data represent means±SEM. (n=3). *p<0.05. (c) Double immunofluorescence staining for SDF-1 and F4/80 (a marker for macrophages) at 5 days after injury. epi, epidermis; we, wound edge. Scale bar: 200 µma.

Semi-quantitative PCR analysis of the granulation tissues showed that mRNA expression of the attractor molecule, stromal cell-derived factor (SDF)-1 and stem cell marker CD133 were significantly increased in the group 4 mice compared to groups 1, 2 and 3 at 5 days after wounding (FIGS. 4a and b) Immunofluorescence staining demonstrated that the number of SDF-1 and F4/80 (a marker of macrophages) positive cells were significantly greater in wound sites in the animals receiving low-dose Tacrolimus alone or with dual drug treatment at 5 days post-injury (FIG. 4c). Interestingly, SDF-1 co-stained with some of the F4/80+ cells indicating that these macrophages were producing or presenting SDF-1 (FIG. 4c; lower panels).

Example 4

Figures 5A, 5B:
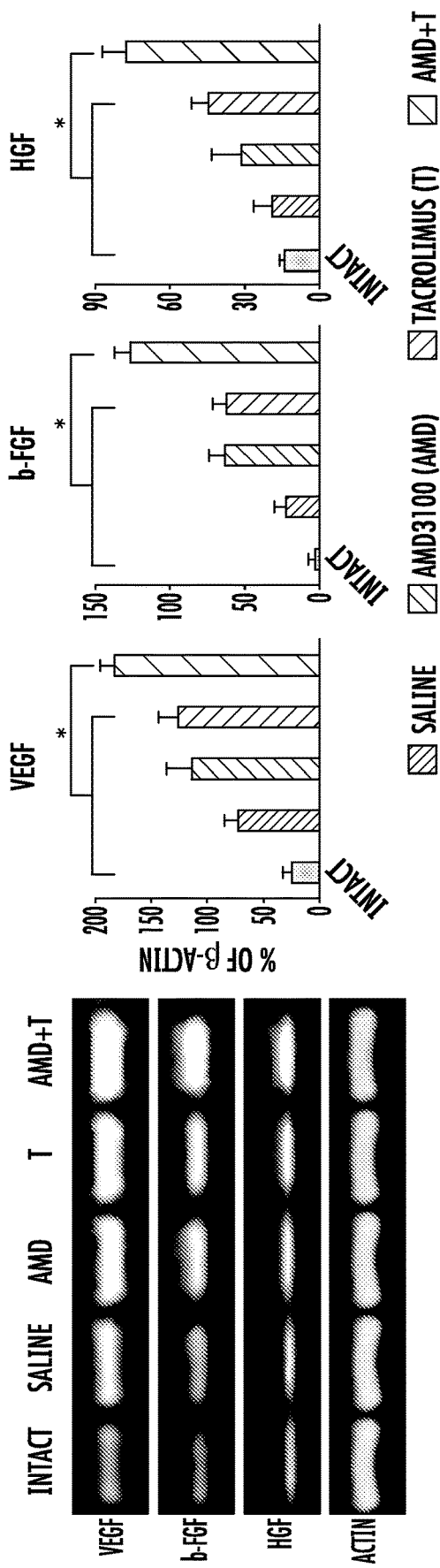
FIG. 5. Increased pro-angiogenic factor expressions in injured mice treated with dual drug therapy. (a) Semi-quantitative PCR analysis of the granulation tissues (day 5) showing the up-regulation of mRNA of VEGF, bFGF and HGF. (b) Graphic representation of increased mRNA expressions determined by calculating growth factor to β-actin ratios. Values represent mean±SEM (n=3). *p<0.05. (c) Double fluorescence staining shows that the major fraction of HGF expressing cells co-stain for the endothelial marker CD31 in granulation tissues (day 5), and that these cells are more abundant in the dual treatment group. Panels in the lower row are stained for α-SMA and show the abundance of these matrix producing cells, paralleling the findings for CD31. epi, epidermis; we, wound edge. Scale bar: 200 µm.

Dual Drug Treatment Increased the Expression of Angiogenic Cytokines at Five Days Post Wounding Semi-quantitative PCR analysis of the granulation tissues showed that mRNA expression of the angiogenic cytokines, vascular endothelial growth factor (VEGF) and basic fibroblast growth factor (b-FGF), and an important stem cell mobilizing and homing factor, hepatocyte growth factor (HGF), were all significantly increased in the group 4 mice compared to group 1, 2 and 3 (FIGS. 5a and b) Immunofluorescence staining demonstrated that the number of HGF positive cells was significantly greater in the granulation tissues recovered from the group 4 mice 5 days post-injury. Similarly, the number of CD31+ endothelial cells in the granulation tissues was markedly increased in the group 4 mice compared to the group 1, 2 and 3. Some of these CD31+ cells formed tube-like structures (FIG. 5c; right panels) in the granulation tissues which also stained for HGF emphasizing the important role of HGF in neovascularization. The tubular structures also co-stained with CD133 (FIG. 3b; right panels) suggesting that HGF may be involved in the differentiation of endothelial cells from CD133 precursors.

Figure 5C:
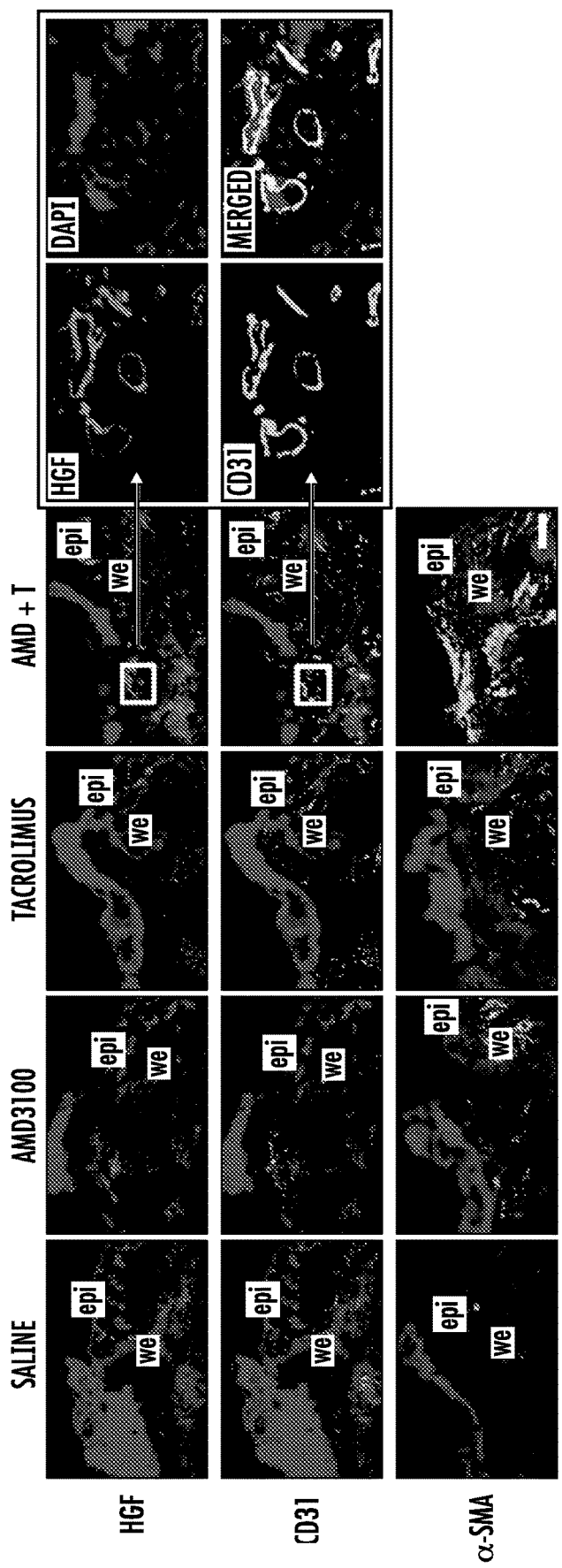

We sought evidence of enhanced production of cells contributing to matrix and indeed immunofluorescence staining demonstrated that the number of α-smooth muscle actin (SMA) positive myofibroblast cells increased in the granulation tissues recovered from the group 2 and 3 mice compared to the group 1, while group 4 mice clearly recruited more myofibroblasts in the granulation tissues at five days (FIG. 5c; lower panels).

Example 5

Lineage Tracing Demonstrated the Critical Role of CD133 Stem Cells in Improving Wound Healing by the Combination of AMD3100 and Low-Dose Tacrolimus Lineage tracing studies were performed to confirm the critical role of CD133 stem cells in wound healing. Adult CD133+/C-L mice containing the Rosa26GFP reporter allele (CD133+/CL X mTmG offspring) were used. CreERT2 activity was induced with tamoxifen 7 days before wounding (FIG. 6a). In this mouse model, progenitor CD133 cells were lacZ positive whereas the CD133 progeny were GFP positive. LacZ and GFP positive cells were observed only in the hair follicles of intact mouse skins (FIG. 6b) as reported by others (Charruyer et al., 2012).

Figure 10:
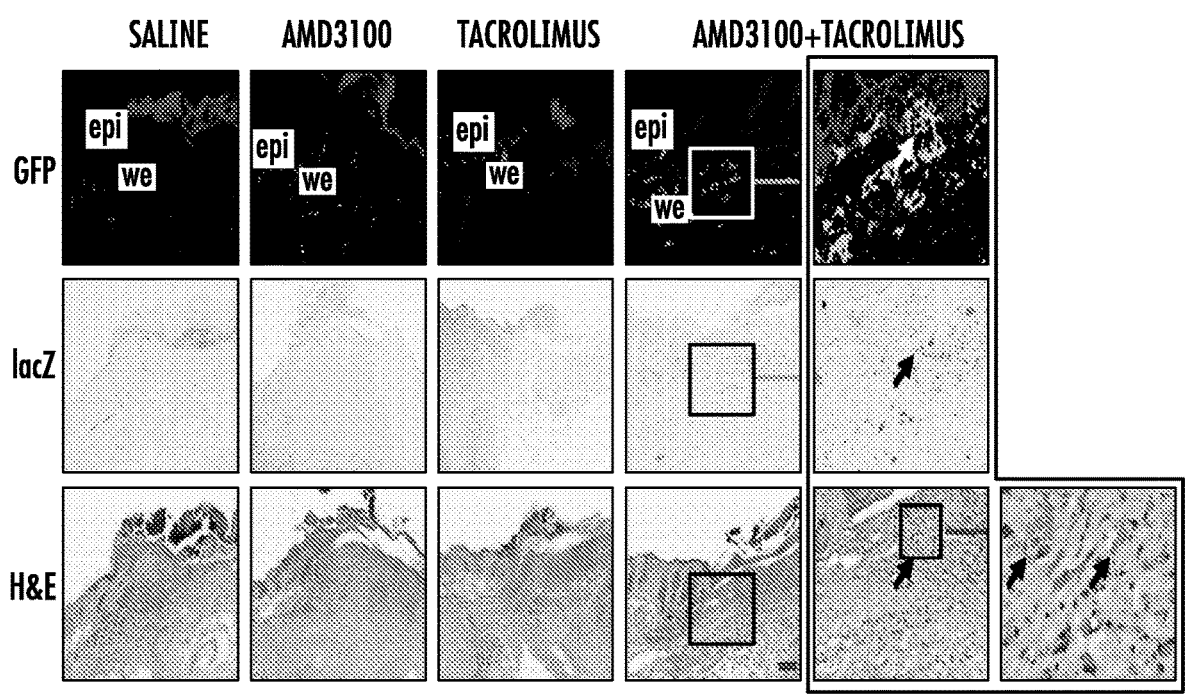
FIG. 10. CD133+ stem cells generate blood vessels in the wounded skin of CD133+/C-L mice in the dual treatment group. Concurrent GFP-fluorescence (upper panels), β-galactosidase (middle panels) and H&E staining (lower panels) of the same section of CD133+/C-L wounds on day 5 post-injury points to CD133+ progenitor cells as one of the sources of newly formed capillaries particularly in the dual treated CD133+/C-L mice. Boxed regions are shown at higher magnification to the right. Arrows point to the GFP+ (upper panel) lacZ+ (middle panel) capillaries (H&E, lower panels) in the same section. epi, epidermis; we, wound edge. Scale bar: 200 µma.

Both lacZ and GFP positive cells were increased in the granulation tissues at 5 days after wounding (FIG. 10; upper and middle panels). The numbers of lacZ and GFP positive cells were significantly higher in the granulation tissues recovered from the group 2 and 3 mice compared to the group 1, but greatest numbers of lacZ and GFP positive cells were found in the granulation tissues of the group 4 mice (FIG. 10). Most of the LacZ positive cells disappeared at 15 days in groups 1, 2 and 3, while their progeny CD133 GFP positive cells remained in the healed tissues (FIG. 6c). However, in group 4 mice newly generated vasculature, epidermis and hair follicles remained positive for both LacZ and GFP (FIG. 6d). These results imply that pharmacologically mobilized CD133 stem cells and their progeny are the principle contributors to skin regeneration.

Discussion

AMD3100 (Plerixafor or Mozobil), is a direct antagonist of CXCR4 and has been used clinically to drive hematopoietic stem cells out of the BM into the peripheral blood of humans where they can be recovered and preserved until the completion of ablative irradiation and/or chemotherapy. AMD3100 has also found application in the repairs of tissue injuries (Jujo et al., 2010, 2013; Nishimura et al., 2012). The injection of a single dose augmented the mobilization of BM derived endothelial progenitor cells (EPCs), which was associated with more rapid neovascularization and functional recovery after myocardial infarction in mice (Jujo et al., 2010). After ischemia/reperfusion injury (Jujo et al., 2013), acute injections redistributed proangiogenic BM cells to ischemic myocardium in an endothelial nitric oxide synthase dependent fashion and promoted the recovery of cardiac function in mice. A single topical application of AMD3100 promoted wound healing in diabetic mice (Nishimura et al., 2012) which was associated with increased cytokine production, increased numbers of bone marrow EPCs, and increased activity of fibroblasts and monocytes/macrophages. Both angiogenesis and vasculogenesis were increased (Nishimura et al., 2012). Our results confirmed and significantly extended those findings. Indeed AMD3100 monotherapy enhanced wound healing to a moderate degree which was associated with a relatively mild recruitment of stem cells to the wound sites (FIG. 3b). Our important contribution is the finding that combining low-dose Tacrolimus with AMD3100 led to a much greater accumulation of stem cells and more rapid regeneration of normal skin in our rodent models of full-thickness skin excision. Tacrolimus given at one tenth the immunosuppressive dose had profound, synergistic effects with AMD3100 in the recruitment of stem cells into the blood stream and wounds, particularly those carrying combined monocyte and SDF-1 markers.

Tacrolimus, is a potent immunosuppressive drug, but surprisingly is also augments cell regeneration and repair in sub-immunosuppressive dosages (Francavilla et al., 1989; Carroll et al., 1994; Gold, 1997). Low dosages (0.1 mg kg-1), but not standard immune-suppressive dosages (1.0 mg kg-1) of Tacrolimus promoted healing of colon anastomoses in rats (Kiyama et al., 2002). Tacrolimus treatment facilitated the healing of lower extremity skin ulcers in a 75-year old woman with lichen planus and diabetes mellitus (Miller, 2008). Bai et al. (Bai et al., 2010) showed in vitro that low (20 ng ml-1)—but not high (2,000 ng ml-1)-dose Tacrolimus treatment skewed BM-derived macrophage polarization towards an active M2 macrophage phenotype. In our study, we also demonstrated that low-dose Tacrolimus improved skin wound healing related to a significant increase in the numbers of SDF-1 producing macrophages in the skin wound on the fifth postoperative day. The messages from such cells contribute to the multiple messages produced by other inflammatory cells and platelets which muster the cells leading to healing. Thus, a strong "push" of stem cells from their BM niches by AMD3100 and a strong "pull" of circulating stem cells by factors in the wound sites enhanced by low-dose Tacrolimus best explains why there was a greater accumulation of stem cells in wound sites and more rapid restoration of normal skin with dual AMD3100/Tacrolimus treatment.

Figure 6E:
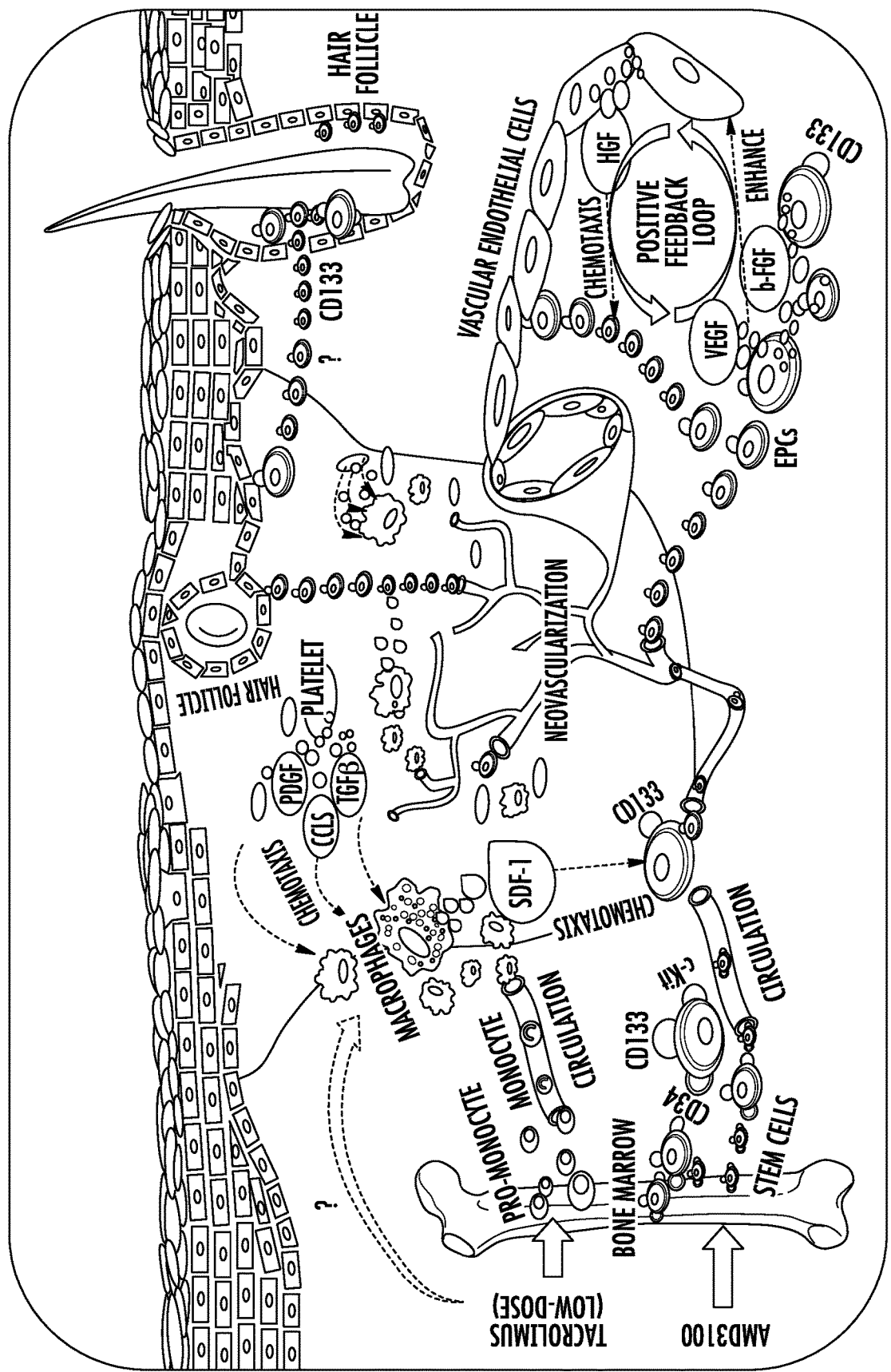
FIG. 6. CD133+ stem cells generate hair follicles and epithelium in the CD133+/C-L mice with dual treatment group. (a) Protocol for analysis of the tamoxifen-induced Cre-dependent GFP expression in CD133-lineage. (b) Intact mouse skin tissues shows marked GFP and CD133 (lacZ+) expression in the hair follicles. (c) Concurrent GFP fluorescence, β-galactosidase (lacZ) and H&E staining of the same section of CD133+/C-L-Rosa26EGFP wounded skin on day 15 post-injury. (d) Higher power photomicrographs. In the boxed areas arrowheads marked the hair follicles in the same section stained for GFP+ (left panel), lacZ+ (middle panel) and H&E (right panel). Arrows point to the GFP and lacZ positive epithelium. epi, epidermis; we, wound edge. Scale bar: 200 µm. (e) Schematic representation of therapeutic mechanism of combination treatment in skin wound healing.

The recruitment of stem cells by dual drugs was associated with elevated expression of VEGF, b-FGF and HGF mRNA in the wounds. Interestingly, anti-HGF antibody co-stained with CD31+ cells that were also CD133+ (FIG. 5c). HGF has many stimulatory actions and has been shown to be a potent regulator of hematopoietic stem and progenitor cells proliferation and differentiation (Nishino et al., 1995), as well as a powerful stimulator of angiogenesis (Ding et al., 2003). It also has been shown that HGF exerts a strong chemotactic effect on MSCs in a wound-healing model (Neuss et al., 2004). Thus, dual drug treatment facilitated the accumulation of SDF-1 producing macrophages which led to the recruitment of more stem cells. In turn the elaboration of HGF, and other autocrine or paracrine mediators produced more proangiogenic factors completing positive feedback loops (FIG. 6e).

CD133 stem cells played a vital role in neovascularization and hair follicle regeneration which is essential for perfect skin regeneration (Sun et al., 2011). Such cells have the potential to differentiate along endothelial lineages in vitro (Hollemann et al., 2012) and are known to migrate to sites of neovascularization in response to mediators (VEGF and SDF-1) Immunofluorescence double staining demonstrated that many CD133 cells co-stained with CD31 (FIG. 2b), an early endothelial cell marker. During the maturation process, the CD133 marker waned and the CD31 phenotype gained (Hollemann et al., 2012). Enhanced angiogenesis was associated with increased numbers of infiltrating CD133+ CD31+ progenitor cells in the wound sites and strengthens the role of these cells in neovascularization.

Epidermal and hair follicle stem cells can undergo reprogramming to become repopulating epidermal progenitor cells following wounding (Ito et al., 2005). Lineage analysis has also demonstrated that follicles can arise from cells outside of the hair follicle stem cell niche, suggesting that cells found in the epidermis can assume a hair follicle stem cell phenotype (Ito et al., 2007). A recent study reported that CD133 is a marker for long-term repopulating murine epidermal stem cells and CD133+ keratinocytes formed both hair follicles and epidermis after injection into immunodeficient mice (Charruyer et al., 2012). It is clear from our lineage tracing studies that increased numbers of CD133 stem cells resulting from dual drug treatment contributed to hair follicle regeneration.

In conclusion, we report here that a novel therapeutic strategy mobilized endogenous stem cells into skin wounds resulting in better and faster healing. The magnitude of both the quantitative and qualitative differences is highly significant and is greater than that found in any other study of wound healing in normal animals. Our studies do not disclose the molecular mechanisms which differentiate these malleable cells into tissue components such as reported for Fgf9 (Gay et al., 2013) or Sept4/ARTS (Fuchs et al., 2013). The interesting finding was that the differentiating steps proceeded faultlessly when there were abundant stem cells resulting in almost normal skin. This is the first report demonstrating the profound synergistic effects of AMD3100 and low dose Tacrolimus in the mobilization, recruitment, and retention of endogenous stem cells leading to faster healing and differentiation into all of the tissues present in normal skin. These findings may be easily applied in the clinic.

Pharmacologic Mobilization of Endogenous Stem Cells Accelerates Skin Wound Healing in Diabetic Rats and Improve Healing of Burn Wounds in Mice Materials and Methods Animals.

Lewis rats and C57BL/6J mice were purchased from the Jackson Laboratory (Bar Harbor, Me.) and maintained in the specific pathogen-free facility of the Johns Hopkins Medical Institutions Animals were cared for according to NIH guidelines and under a protocol approved by the Johns Hopkins University Animal Care Committee.

Diabetic Rat Model.

Streptozotocin (STZ) is an antibiotic that can cause pancreatic beta-cell destruction, so it is widely used experimentally as an agent capable of inducing insulin-dependent diabetes mellitus (IDDM), also known as type 1 diabetes mellitus (T1DM). The most common animal model of human diabetes is streptozotocin (STZ)-induced diabetes in the rat. Streptozotocin (STZ)-induced diabetic rat model used to determine the skin wound healing. All rats (aged at 12-16 weeks) developed diabetes (blood glucose >450 mg/dL) 2 weeks after STZ injection (50 mg/kg, i.p.). The four excisional wounds were placed 1 cm to either side of the midline and 1 cm above and below the midpoint between the costal margin and the iliac crests. The sterile disposable biopsy punch (5 mm in diameter; Miltex) was aligned vertically over the center of the mark and punched through the skin and panniculus carnosus by applying pressure and twisting at the same time. The same procedure was repeated, generating four wounds on each animal.

Burn Wound Model in Mice.

Mice aged 24-30 months were anesthetized with 3% isoflurane (Baxter Healthcare Co., Deerfield, Ill., USA) using an anesthesia machine, shaved on the dorsum and depilated with Nair cream (Church & Dwight Co., Princeton, N.J., USA). The burn wound was generated as previously reported (*Arch Surg* 2010; 145: 259-266). Briefly, a custom made 100-g aluminum rod was heated in a 100° C. water bath for 5 min. One burns of 1.2-cm diameter were produced on the dorsum of each mouse. To assure burn uniformity, only the weight of the rod provided pressure to the skin surface. Contact time of 4 s measured with a metronome was chosen to produce a standardized full-thickness burn. The burns were third degree including destruction of the skin, subcutaneous tissue and the panniculous carnosus. Buprenorphine (0.1 mg/kg) was administrated subcutaneously for analgesia.

Treatment and Wound Measurement.

The animals were house singly after regaining consciousness and injected subcutaneously with AMD3100 (AMD) (1.0 mg/kg, every two days, Sigma-Aldrich, St Louis, Mo.) or/and Tacrolimus (T) (0.1 mg/kg, daily, purchased from Pharmacy at Johns Hopkins hospital) from day 0 to the day of complete closure.

Each wound site was digitally photographed at the indicated time intervals, and wound areas were determined on photographs using Adobe Photoshop (version 7.0; Adobe Systems, San Jose, Calif.). Changes in wound areas over time were expressed as the percentage of the initial wound areas. All wound evaluations were double blinded.

Results

Example 6

Figure 11:
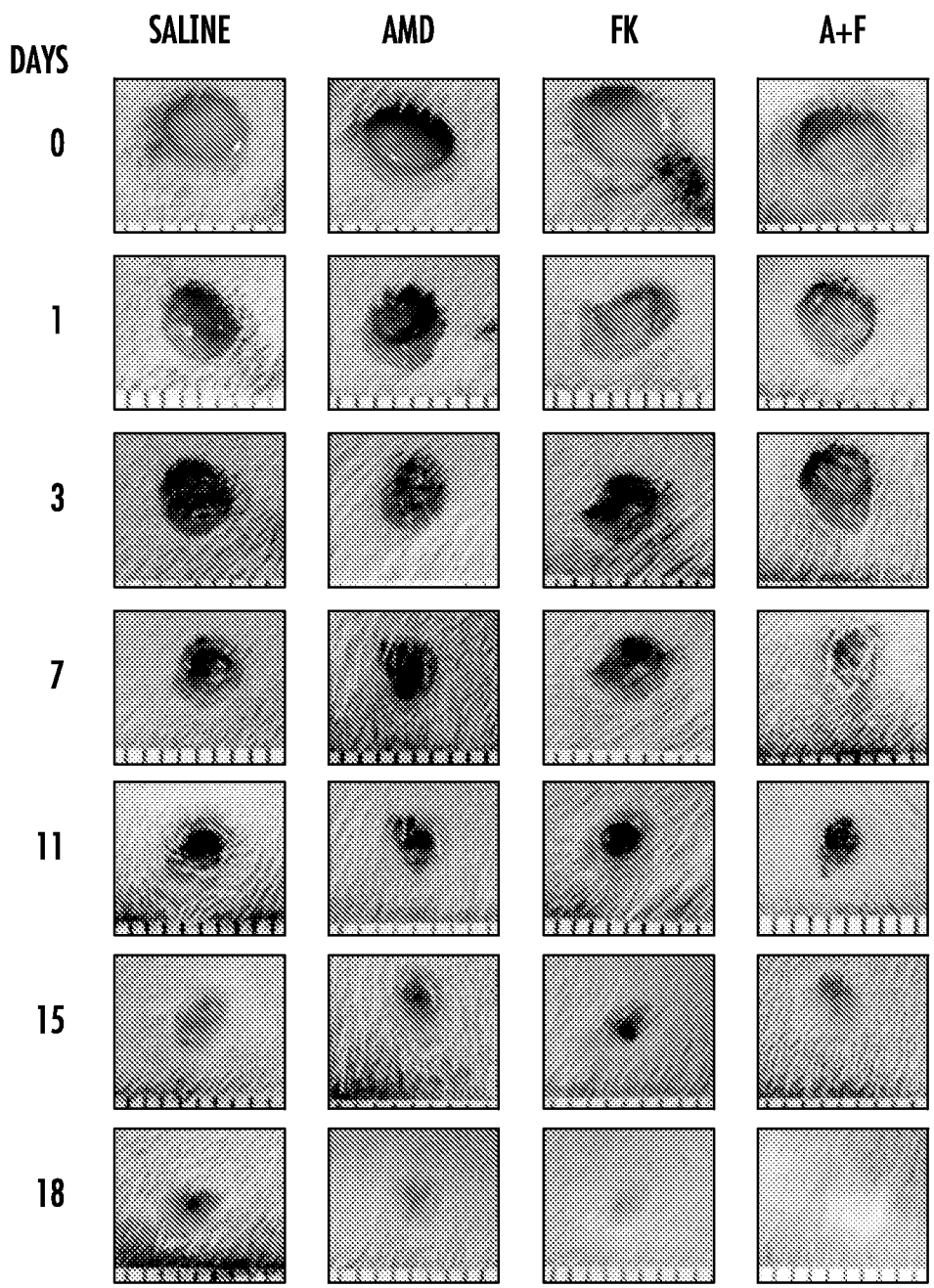
FIG. 11. Gross and microscopic time course photographs of burned skin following treatment with saline, treatment with low-dose tacrolimus (0.1 mg/kg/dose) alone, AMD3100 (1.0 mg/kg/dose) monotherapy or a combination of low-dose tacrolimus and AMD3100. Representative photographs of skin wounds in diabetic rats (n=4 or 5) showing a notable effect of the combined therapy on the enhancement of wound healing.

AMD3100 Plus Low-Dose Tacrolimus Accelerated Skin Wound Healing in Diabetic Rats Wounds reached complete closure on day 18 after surgery in the control group of non-diabetic rats, which is consistent with the known healing kinetics in this established model. However, healing was significantly delayed in diabetics rats treated with saline as wounds reached complete closure on day 23 after surgery. The animals (n=4 or 5) treated with Tacrolimus or AMD3100 alone exhibited significantly but only moderately faster healing compared to the saline control group as wounds reached complete closure at day 21. The healing time was reduced to 18 days or by 22% in the diabetic rats treated with AMD3100 plus low-dose Tacrolimus. Digital images showed that treatment with dual drug therapy had significant effects reducing the size of the skin defect as soon as day seven (FIG. 11).

Example 7

AMD3100 Plus Low-Dose Tacrolimus Improved Healing of Burn Wounds in Mice

Figure 12A:
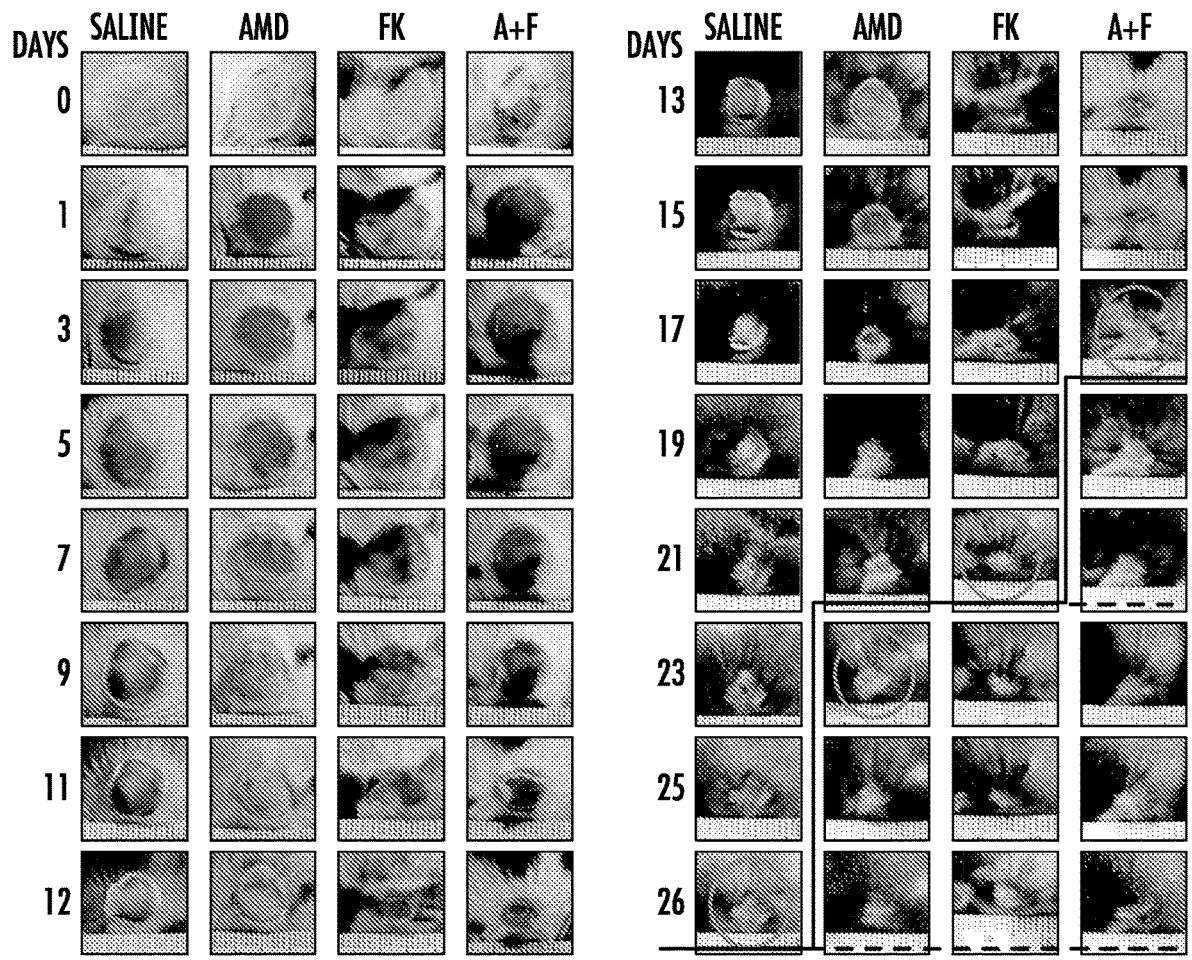
FIG. 12. Combined therapy with low-dose Tacrolimus and AMD3100 improved wound closure after burn injury in mice. (a) Gross and microscopic time course photographs of burned skin following treatment with saline, treatment with low-dose tacrolimus (0.1 mg/kg/dose) alone, AMD3100 (1.0 mg/kg/dose) monotherapy or a combination of low-dose tacrolimus and AMD3100. Representative photographs of burned skin in mice (n=7) showing a notable effect of the combined therapy on the enhancement of burn wound. (b) Quantification of the wound area at consecutive days following burn injury. Mean±SEM (n=7) is shown. *p<0.05 dual treated vs. vehicle treated mice. (c) Wound closure was analyzed with Kaplan-Meier survival analysis (n=7).
Figure 12B:
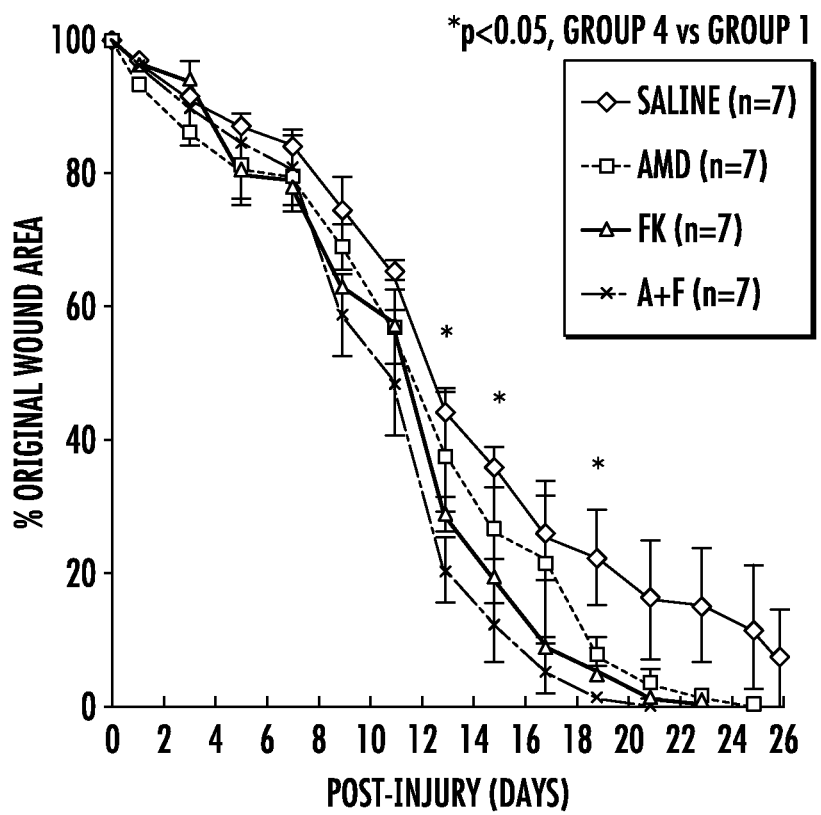
Figure 12C:
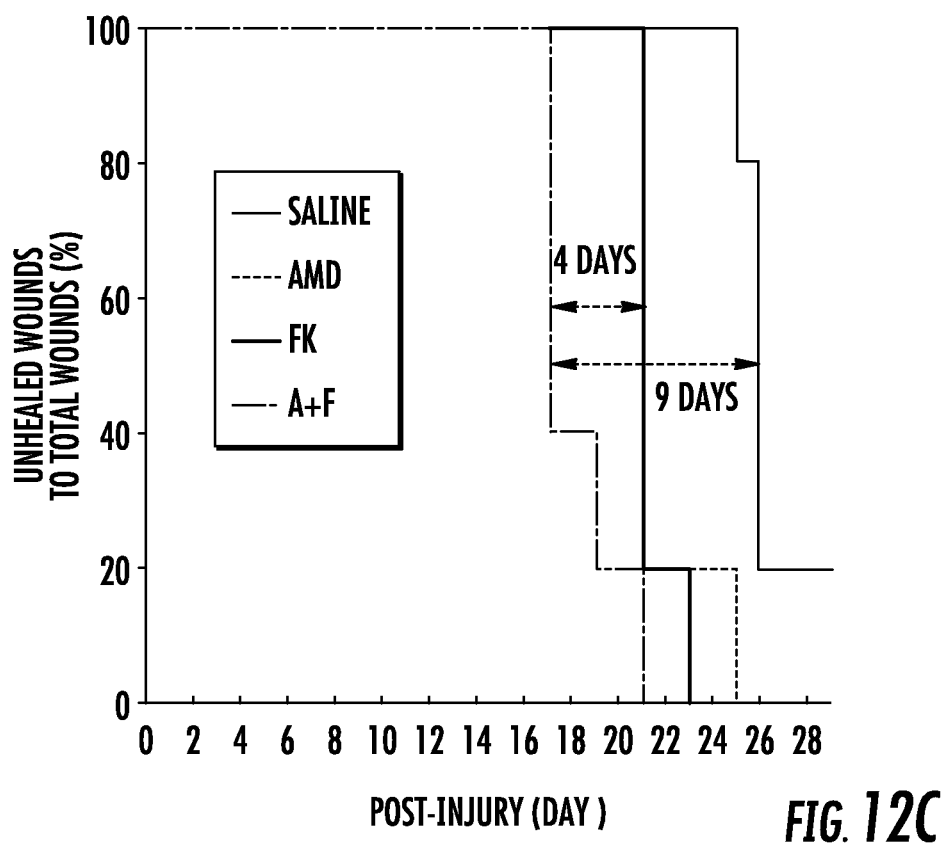
Figure 13:
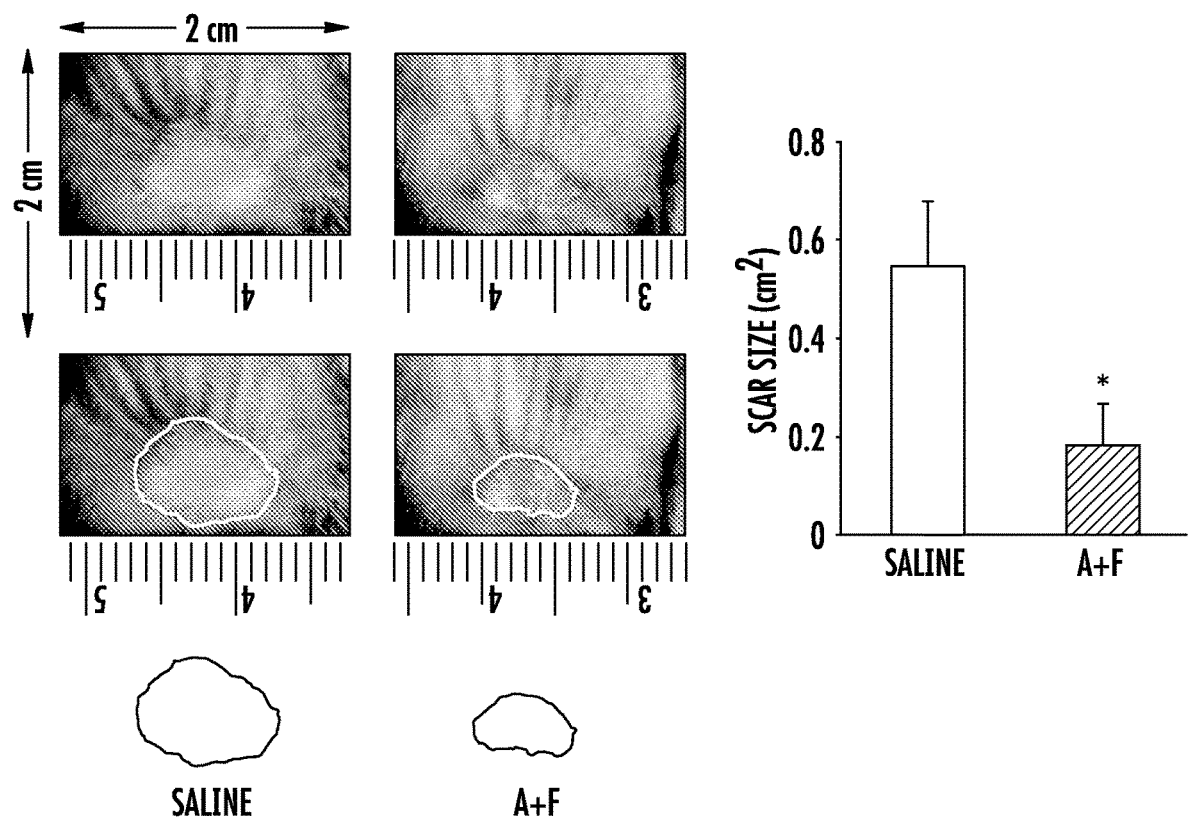
FIG. 13. Dual drug treatment reduced scar formation post burn. Scar size of saline and dual drug-treated mice at 60 days post-burn (1.44 cm2) (n=3); photograph (left panels) and quantification (right panel) are shown. Solid line indicates scar border. *P<0.05.

Skin lesions were analyzed at different time-points by measuring the wound area. Wounds reached complete closure on day 26 after burn injury in control (saline) group (n=7, 5 C57BL/6J+2 129S1/SvImJ mice) Animals treated with Tacrolimus or AMD3100 alone exhibited significantly accelerated wound closure compared to the saline control group as wounds reached complete closure at day 21 and 23, respectively. Interestingly, the reduction of the wound area in the mice treated with AMD3100 plus low-dose Tacrolimus was even more potent, starting already from day 13. At day 17, all wounds in this combined treatment group were covered with epithelium and considered closed, demonstrating striking effects of combined therapy on burn wound healing (FIG. 12). Dual drug treatment also significantly reduced scar formation at 2 months post-burn (FIG. 13).

CONCLUSION

In summary, we confirmed that the wound healing aspect indeed apply to diabetic rats and a mouse burn injury model. The results demonstrated that pharmacologic mobilization of endogenous stem cells accelerates skin wound healing in diabetic rats (The healing time was reduced to 18 days (from 23 days) or by 22%) and improve healing of burn wounds in mice (The healing time was reduced to 17 days (from 26 days) or by 34%). We believe that the principles discovered in our studies have important implications in tissue repair and regeneration.

We claim:

1. A method of recruitment of SDF-producing macrophages comprising administering to a human patient who is diabetic or has a burn injury and is in need of external wound treatment a therapeutically effective amount of a stem cell mobilizer and a low dose of Tacrolimus, and the low dose is in a range of about 0.004 mg/kg to about 0.008 mg/kg, and wherein the stem cell mobilizer and the Tacrolimus are administered simultaneously to the patient about once every two days, wherein, after the administration, the patient's external wound healing is improved as compared to prior to the administration, wherein the patient is diabetic or has a burn injury, and wherein administration of the Tacrolimus and the stem cell mobilizer promotes granulation tissue formation, tissue regeneration and re-epithelialization of the wound, and wherein administration of the Tacrolimus and the stem cell mobilizer recruits SDF-producing macrophages.

2. The method of claim 1, wherein the stem cell mobilizer is selected from the group consisting of AMD3100, AMD3465, TG-0054, BKT140, G-CSF, GM-CSF, SDF-1, and SCF.

3. The method of claim 1, wherein the stem cell mobilizer is a CXCR4 antagonist.

4. The method of claim 3, wherein the stem cell mobilizer is AMD3100.

5. A method of recruitment of SDF-producing macrophages comprising administering to a human patient who is diabetic or has a burn injury and is in need of external wound treatment a therapeutically effective amount of AMD3100 and a low dose of Tacrolimus, wherein the low dose is in a range of about 0.004 mg/kg to about 0.008 mg/kg, and wherein the AMD3100 and the Tacrolimus are administered simultaneously to the patient about once every two days, wherein, after the administration, the patient's external wound healing is improved as compared to prior to the administration, wherein the patient is diabetic or has a burn injury, and wherein administration of the Tacrolimus and the AMD3100 promotes granulation tissue formation, tissue regeneration and re-epithelialization of the wound, and wherein administration of the Tacrolimus and the AMD3100 recruits SDF-producing macrophages.

6. A method of recruitment of SDF-producing macrophages comprising administering to a human patient who is diabetic or has a burn injury and is in need of external wound treatment and is in need of external wound treatment a therapeutically effective amount of an agent that mobilizes $CD34^+$ and/or $CD133^+$ stem cells and a low dose of Tacrolimus, and the low dose is in a range of about 0.004 mg/kg to about 0.008 mg/kg, and wherein the agent that mobilizes $CD34^+$ and/or $CD133^+$ stem cells and the Tacrolimus are administered simultaneously to the patient about once every two days, wherein, after administration, the patient's external wound healing is improved as compared to prior to the administration, wherein the patient is diabetic or has a burn injury, and wherein administration of the Tacrolimus and the agent that mobilizes $CD34^+$ and/or $CD133^+$ stem cells promotes granulation tissue formation, tissue regeneration and re-epithelialization of the wound, and wherein administration of the Tacrolimus and the agent that mobilizes $CD34^+$ and/or $CD133^+$ stem cells recruits SDF-producing macrophages.

7. The method of claim 6, wherein the agent that mobilizes $CD34^+$ and/or $CD133^+$ stem cells is AMD3100.

8. A method of recruitment of SDF-producing macrophages comprising administering to a human patient who is diabetic or has a burn injury and is in need of external wound treatment and is in need of external wound treatment a low dose of Tacrolimus in an amount sufficient to mobilize stem cells to the peripheral blood of the recipient and a second agent to mobilize stem cells to the peripheral blood, wherein the low dose of Tacrolimus is in a range of about 0.004 mg/kg to about 0.008 mg/kg, and wherein the Tacrolimus and the second agent are administered to the patient simultaneously about once every two days, wherein, after administration, the patient's external wound healing is improved as compared to prior to the administration, wherein the patient is diabetic or suffers from a burn injury, and wherein administration of the Tacrolimus and the second agent promotes granulation tissue formation, tissue regeneration and re-epithelialization of the wound, and wherein administration of the Tacrolimus and the second agent recruits SDF-producing macrophages.

9. The method of claim 8, wherein the stem cell mobilizer is selected from the group consisting of AMD3100, AMD3465, TG-0054, BKT140, G-CSF, GM-CSF, SDF-1, and SCF.

10. The method of claim 8, wherein the stem cell mobilizer is a CXCR4 antagonist.

11. The method of claim 8, wherein the stem cell mobilizer is AMD3100.

12. A method of recruitment of SDF-producing macrophages comprising administering a low dose of Tacrolimus to a human patient who is diabetic or has a burn injury and is in need of external wound treatment in an amount sufficient to mobilize $CD34^+$ and/or $CD133^+$ stem cells to the peripheral blood, wherein the low dose is in a range of about 0.004 mg/kg to about 0.008 mg/kg, and administering a stem cell mobilizer, wherein the Tacrolimus and the stem cell mobilizer are administered to the patient simultaneously about once every two days, wherein, after administration, the patient's external wound healing is improved as compared to prior to the administration, wherein the patient is diabetic or has a burn injury, and wherein administration of the Tacrolimus and the stem cell mobilizer promotes granulation tissue formation, tissue regeneration and re-epithelialization of the wound, and wherein administration of the Tacrolimus and the stem cell mobilizer recruits SDF-producing macrophages.

\* \* \* \* \*

```
                       SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Forward primer for mouse SDF-1

<400> SEQUENCE: 1
gacggtaaac cagtcagcct                                              20

<210> SEQ ID NO 2
<211> LENGTH: 24
<212> TYPE: DNA
<213> ORGANISM: Artificial Sequence
<220> FEATURE:
<223> OTHER INFORMATION: Reverse primer for mouse SDF-1

<400> SEQUENCE: 2
cacacttgtc tgttgttgtt cttc                                         24

<210> SEQ ID NO 3
<211> LENGTH: 20
<212> TYPE: DNA
<213> ORGANISM: Artificial Sequence
<220> FEATURE:
<223> OTHER INFORMATION: Forward primer for mouse CD133

<400> SEQUENCE: 3
tccagcaaac aagcaacaag                                              20

<210> SEQ ID NO 4
```

```
<211> LENGTH: 19
<212> TYPE: DNA
<213> ORGANISM: Artificial Sequence
<220> FEATURE:
<223> OTHER INFORMATION: Reverse primer for mouse CD133

<400> SEQUENCE: 4
cctatgccga accagaaca                                                    19

<210> SEQ ID NO 5
<211> LENGTH: 20
<212> TYPE: DNA
<213> ORGANISM: Artificial Sequence
<220> FEATURE:
<223> OTHER INFORMATION: Forward primer for mouse VEGF

<400> SEQUENCE: 5
cactggaccc tggctttact                                                   20

<210> SEQ ID NO 6
<211> LENGTH: 20
<212> TYPE: DNA
<213> ORGANISM: Artificial Sequence
<220> FEATURE:
<223> OTHER INFORMATION: Reverse primer for mouse VEGF

<400> SEQUENCE: 6
ggtgatgttg ctctctgacg                                                   20

<210> SEQ ID NO 7
<211> LENGTH: 18
<212> TYPE: DNA
<213> ORGANISM: Artificial Sequence
<220> FEATURE:
<223> OTHER INFORMATION: Forward primer for mouse b-FGF

<400> SEQUENCE: 7
caagggagtg tgtgccaa                                                     18

<210> SEQ ID NO 8
<211> LENGTH: 18
<212> TYPE: DNA
<213> ORGANISM: Artificial Sequence
<220> FEATURE:
<223> OTHER INFORMATION: Reverse primer for mouse b-FGF

<400> SEQUENCE: 8
tgcccagttc gtttcagt                                                     18

<210> SEQ ID NO 9
<211> LENGTH: 20
<212> TYPE: DNA
<213> ORGANISM: Artificial Sequence
<220> FEATURE:
<223> OTHER INFORMATION: Forward primer for mouse HGF

<400> SEQUENCE: 9
atgagagagg cgaggagaag                                                   20

<210> SEQ ID NO 10
<211> LENGTH: 19
<212> TYPE: DNA
<213> ORGANISM: Artificial Sequence
<220> FEATURE:
<223> OTHER INFORMATION: Reverse primer for mouse HGF

<400> SEQUENCE: 10
```

```
gtagcgccag ccgtaaata                                              19

<210> SEQ ID NO 11
<211> LENGTH: 21
<212> TYPE: DNA
<213> ORGANISM: Artificial Sequence
<220> FEATURE:
<223> OTHER INFORMATION: Forward primer for mouse Beta-actin

<400> SEQUENCE: 11
tggcaccaca ccttctacaa t                                           21

<210> SEQ ID NO 12
<211> LENGTH: 20
<212> TYPE: DNA
<213> ORGANISM: Artificial Sequence
<220> FEATURE:
<223> OTHER INFORMATION: Reverse primer for mouse Beta-actin

<400> SEQUENCE: 12
accagaggca tacagggaca                                             20
```